US010024792B2

(12) United States Patent
Toivola et al.

(10) Patent No.: US 10,024,792 B2
(45) Date of Patent: Jul. 17, 2018

(54) REMOVABLE CHROMATIC WITNESS ASSEMBLY, SYSTEM, AND METHOD TO MONITOR THERMAL EVENTS AND IMPACT EVENTS ON A COMPOSITE STRUCTURE

(71) Applicants: The Boeing Company, Chicago, IL (US); University of Washington, Seattle, WA (US)

(72) Inventors: Ryan E. Toivola, Kirkland, WA (US); Alex Kwan-Yue Jen, Kenmore, WA (US); Sei-Hum Jang, Mukilteo, WA (US); Brian D. Flinn, Seattle, WA (US); Eric G. Winter, Freeland, WA (US); Gary E. Georgeson, Tacoma, WA (US); Wesley L. Holman, Mill Creek, WA (US); Gregory R. Gleason, Seattle, WA (US); Scott R. Johnston, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 72 days.

(21) Appl. No.: 15/231,691

(22) Filed: Aug. 8, 2016

(65) Prior Publication Data
US 2018/0038792 A1 Feb. 8, 2018

(51) Int. Cl.
G01N 21/64 (2006.01)
B32B 7/12 (2006.01)
(Continued)

(52) U.S. Cl.
CPC ............. G01N 21/645 (2013.01); B32B 7/12 (2013.01); B32B 37/12 (2013.01); B64F 5/60 (2017.01);
(Continued)

(58) Field of Classification Search
CPC ....... G01N 33/442; G01N 21/64; G01B 11/16
See application file for complete search history.

(56) References Cited

U.S. PATENT DOCUMENTS 6,200,508 B1  3/2001 Jacobson et al.
8,691,383 B2  4/2014 Georgeson et al.
(Continued)

OTHER PUBLICATIONS

Jennifer A. Lewis et al., Direct Writing in Three Dimensions, article published in materialstoday, vol. 7, Issues 7-8, URL: http://www.sciencedirect.com/science/article/pii/S136970210400344X, Jul./Aug. 2004, 8 pages.
(Continued)

Primary Examiner — Casey Bryant

(57) ABSTRACT

There is provided a removable chromatic witness assembly, system, and method to monitor thermal events and impact events on a surface of a composite structure. The removable chromatic witness assembly has a plurality of chromatic witness geometric configurations separately coupled in an arrangement to one or more portions of a polymeric film layer. Each chromatic witness geometric configuration has a plurality of chromatic probes of a same type incorporated into an adhesive material. At least two of the geometric configurations have a different type of chromatic probes with a different sensing capability for thermal events and impact events on the composite structure. The polymeric film layer and the geometric configurations form the removable chromatic witness assembly in a form of a removable chromatic witness applique configured to be removably applied directly and continuously to the surface of the composite structure, and configured to monitor the thermal and impact events.

24 Claims, 16 Drawing Sheets

(51) Int. Cl.
  *B32B 37/12* (2006.01)
  *G01L 1/24* (2006.01)
  *G01K 11/12* (2006.01)
  *B64F 5/60* (2017.01)

(52) U.S. Cl.
  CPC ............... *G01K 11/12* (2013.01); *G01L 1/24* (2013.01); *B32B 2307/412* (2013.01); *B32B 2605/18* (2013.01); *G01N 2201/061* (2013.01); *G01N 2201/062* (2013.01)

(56) References Cited

U.S. PATENT DOCUMENTS

| | | | |
|---|---|---|---|
| 8,720,278 B1 * | 5/2014 | Toivola | G01B 11/16 73/762 |
| 9,085,052 B1 | 7/2015 | Georgeson et al. | |
| 9,372,177 B2 | 6/2016 | Georgeson et al. | |
| 2004/0151978 A1 | 8/2004 | Huang | |
| 2012/0060594 A1 * | 3/2012 | Care | H01J 61/34 73/112.01 |
| 2014/0273240 A1 | 9/2014 | Georgeson et al. | |
| 2014/0328369 A1 * | 11/2014 | Flinn | G01N 33/442 374/57 |
| 2015/0308907 A1 | 10/2015 | Georgeson et al. | |
| 2015/0338296 A1 | 11/2015 | Georgeson et al. | |
| 2016/0025662 A1 | 1/2016 | Georgeson et al. | |
| 2016/0146747 A1 | 5/2016 | Degaetano et al. | |
| 2016/0195437 A1 | 7/2016 | Georgeson et al. | |
| 2016/0195470 A1 | 7/2016 | Safai et al. | |

OTHER PUBLICATIONS

U.S. Patent and Trademark Office, U.S. Appl. No. 14/670,394, filed Mar. 26, 2015, Degaetano et al., which is another application of applicant The Boeing Company.

U.S. Patent and Trademark Office, U.S. Appl. No. 14/856,550, filed Sep. 16, 2015, Georgeson et al., which is another application of applicant The Boeing Company.

* cited by examiner

REMOVABLE CHROMATIC WITNESS ASSEMBLY, SYSTEM, AND METHOD TO MONITOR THERMAL EVENTS AND IMPACT EVENTS ON A COMPOSITE STRUCTURE

CROSS REFERENCE TO RELATED APPLICATION

This nonprovisional patent application is related to contemporaneously filed U.S. nonprovisional patent application Ser. No. 15/231,557, titled "SYSTEMS FOR MONITORING THE ENVIRONMENTAL HISTORY OF A COMPONENT", filed on Aug. 8, 2016.

BACKGROUND

1) Field of the Disclosure

The disclosure relates generally to systems and methods for monitoring and evaluating composite structures, and more particularly, to systems and methods for monitoring and evaluating thermal events and mechanical impact events on a surface of a composite structure, such as an aircraft composite structure.

2) Description of Related Art

Composite structures may be used in a wide variety of applications, including in the manufacture of aircraft, spacecraft, rotorcraft, watercraft, automobiles, and other vehicles and structures, due to their high strength-to-weight ratios, corrosion resistance and other favorable properties. In particular, in aircraft construction, composite structures may be used to form the tail sections, wings, fuselage and other component parts of the aircraft.

During manufacturing of composite structures or parts, such as composite aircraft structures or parts, it is important to understand and control a thermal profile and a uniform temperature distribution over an entire area of the composite structure or part, and to identify any areas experiencing thermal issues or mechanical impact issues. A Thermal Protection System (TPS), such as insulation blankets, may be used to insulate propulsion system structures or parts, such as the inner walls of an engine cowling or cover, that may be exposed to high temperatures and high heat (e.g., greater than 250° F. (degrees Fahrenheit)). When high heat penetrates the TPS, the TPS may not function properly, or as designed, and may result in service issues.

To monitor a composite structure or part or the TPS, known systems and methods exist that use multiple thermocouples mounted at various locations on a composite structure or part to measure temperatures at the various locations during flight testing, ground testing, and/or in-service monitoring. However, with such known systems and methods, the thermocouples may only measure the temperatures at specific point locations and may not measure out-of-range temperature information at other locations. Coverage depends upon how many thermocouples are used, and it may be difficult or impractical to provide full coverage temperature monitoring and thermal mapping using only thermocouples. For example, positioning of multiple thermocouples on large or complex structures or parts may result in increased time and labor to install. Moreover, removal of the thermocouples may produce mark-off, such as resin pockets, resin "bumps", wrinkles, or geometry issues, on the resulting manufactured structure or part.

Moreover, other known systems and methods for monitoring composite structures, such as known thermal measurement coatings, may not have the range or precision of thermal monitoring needed, may not be easily applied or removed, and may not be easily manufactured in sufficient quantities for effective use by test programs. In addition, such known thermal measurement coatings may not be able to be applied continuously and evenly with full contact onto the surface of the composite structure, and may not be removable or easily removed for analysis and processing of its response.

Accordingly, there is a need in the art for an improved assembly, system, and method for monitoring thermal events and impact events on a surface of a composite structure that provide advantages over known systems and methods.

SUMMARY

Example implementations of this disclosure provide an improved assembly, system, and method to monitor thermal events and impact events on a surface of a composite structure. As discussed in the below detailed description, embodiments of the improved assembly, method, and system may provide significant advantages over existing systems and methods for monitoring thermal events and impact events on a surface of a composite structure.

In addition, example implementations of this disclosure provide an improved assembly, system, and method to monitor thermal events and impact events on a surface of a composite structure or part during flight testing, ground testing, in-service monitoring, or other testing and monitoring. As discussed in the below detailed description, embodiments of the improved assembly, method, and system may provide significant advantages over existing systems and methods for monitoring thermal and impact events relating to composite structures or parts.

In one embodiment there is provided a removable chromatic witness assembly to monitor thermal events and impact events on a surface of a composite structure. The removable chromatic witness assembly comprises a plurality of chromatic witness geometric configurations separately coupled in a repeating arrangement to one or more portions of a polymeric film layer.

Each chromatic witness geometric configuration comprises a plurality of chromatic probes of a same type incorporated into an adhesive material. At least two of the plurality of chromatic witness geometric configurations have a different type of chromatic probes with a different sensing capability for one of, thermal events and impact events on the surface of the composite structure.

The polymeric film layer and the plurality of chromatic witness geometric configurations form the removable chromatic witness assembly in a form of a removable chromatic witness applique configured to be removably applied directly and continuously to the surface of the composite structure, and configured to monitor the thermal events and the impact events on the surface of the composite structure.

In another embodiment there is provided a removable chromatic witness system to monitor thermal events and impact events on a surface of a composite structure. The removable chromatic witness system comprises the composite structure having a surface to be tested and monitored for one of, the thermal events and the impact events.

The removable chromatic witness system further comprises a removable chromatic witness assembly comprising a removable chromatic witness applique applied directly and continuously over the surface of the composite structure to be tested and monitored. The removable chromatic witness assembly comprises a plurality of chromatic witness geometric configurations separately coupled in a repeating arrangement to one or more portions of a polymeric film layer. Each chromatic witness geometric configuration comprises a plurality of chromatic probes of a same type incorporated into an adhesive material, and at least two of the plurality of chromatic witness geometric configurations having a different type of chromatic probes with a different sensing capability for sensing one of, the thermal events and the impact events on the surface of the composite structure.

The removable chromatic witness system further comprises a light source configured to activate the plurality of chromatic probes in the removable chromatic witness applique applied to the composite structure. Each different type of chromatic probe is configured to fluoresce in a different predefined time-temperature range.

The removable chromatic witness system further comprises an imaging device configured to image and record one or more images of a chromatic response of the different types of chromatic probes to the light source. The chromatic response comprises one or more color changes and one or more intensity changes.

The removable chromatic witness system further comprises a data processor system configured for processing and analyzing the one or more images to identify any areas on the surface of the composite structure that have experienced one of, temperatures above a predefined threshold temperature, and impacts above a predefined threshold impact, based on the chromatic response.

In another embodiment there is provided a method of using a removable chromatic witness system to monitor thermal events and impact events on a surface of a composite structure. The method comprises the step of providing the removable chromatic witness system.

The removable chromatic witness system comprises the composite structure having the surface to be tested and monitored for one of, thermal events and impact events. The removable chromatic witness system further comprises a removable chromatic witness assembly comprising a removable chromatic witness applique having a plurality of chromatic witness geometric configurations separately coupled in a repeating arrangement to one or more portions of a polymeric film layer. Each chromatic witness geometric configuration comprises a plurality of chromatic probes of a same type incorporated into an adhesive material. At least two of the plurality of chromatic witness geometric configurations have a different type of chromatic probes with a different sensing capability for sensing one of, the thermal events and the impact events on the surface of the composite structure. The removable chromatic witness system further comprises a light source, an imaging device, and a data processor system.

The method further comprises the step of applying the removable chromatic witness applique directly and continuously over the surface of the composite structure to be tested and monitored. The method further comprises the step of testing the composite structure with the applied removable chromatic witness applique, by exposing for a predefined time period the composite structure with the applied removable chromatic witness applique, to one of, one or more temperatures, and one or more impacts.

The method further comprises the step of illuminating with the light source the removable chromatic witness applique, to activate the different types of chromatic probes to fluoresce in different predefined time-temperature ranges, in response to the light source. The method further comprises the step of obtaining with the imaging device one or more images of a chromatic response of the different types of chromatic probes to the light source. The chromatic response comprises one or more color changes and one or more intensity changes.

The method further comprises the step of using the data processor system to identify areas on the surface of the composite structure that have experienced one of, temperatures above a predefined threshold temperature, and impacts above a predefined threshold impact, based on the chromatic response.

In another embodiment there is provided a method of making a removable chromatic witness assembly to monitor thermal events and impact events on a surface of a composite structure. The method comprises the step of mixing a plurality of chromatic probes with an adhesive material to form separate chromatic witness geometric configurations. The plurality of chromatic probes comprises at least a first series of chromatic probes, a second series of chromatic probes, and a third series of chromatic probes.

The method further comprises the step of applying a polymeric film layer over each of the chromatic witness geometric configurations to form multiple removable chromatic witness assemblies. The method further comprises the step of dividing each of the removable chromatic witness assemblies into multiple, separate rectangular strips.

The method further comprises the step of applying the rectangular strips in an adjacent repeating arrangement over a backing film layer. The method further comprises the step of applying a pressure sensitive adhesive (PSA) layer to the backing film layer having the attached chromatic witness geometric configurations and the polymeric film layers to form the removable chromatic witness assembly comprising a removable chromatic witness applique configured for application over the surface of the composite structure.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

Figure 1A:
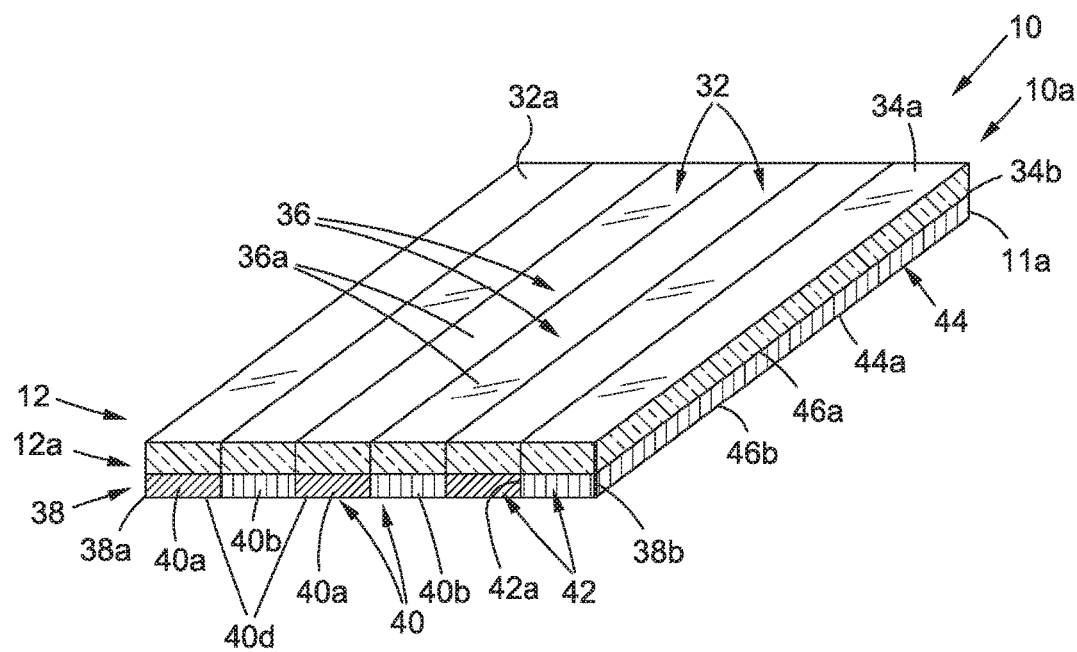
FIG. 1A is a schematic illustration of a cross-sectional perspective view of an embodiment of a removable chromatic witness assembly of the disclosure.

The figures shown in this disclosure represent various aspects of the embodiments presented, and only differences will be discussed in detail.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and fully convey the scope of the disclosure to those skilled in the art.

Now referring to the Figures, FIGS. 1A-6 show cross-sectional perspective views of exemplary embodiments of a removable chromatic witness assembly 10 of the disclosure. In one embodiment, there is provided the removable chromatic witness assembly 10 (see FIGS. 1A-6) to monitor thermal events 18 (see FIG. 8) and impact events 20 (see FIG. 8) on a surface 16 (see FIG. 8) of a composite structure 14 (see FIGS. 1C, 2C, 3C, 4C, 8, 13), such as an aircraft composite structure 14a (see FIGS. 1C, 2C, 3C, 4C, 8, 13). The thermal events 18 (see FIG. 8) include, but are not limited to, exposure of the surface 16 (see FIG. 8) of the composite structure 14 (see FIGS. 1C, 2C, 3C, 4C, 8, 13) to high temperatures (e.g., 130° F.-500° F., or greater), or thermal loads. The impact events 20 (see FIG. 8) include, but are not limited to, mechanical impacts, or mechanical impact loads or force (e.g., 0.5 Joules to 10 Joules), made to the surface 16 (see FIG. 8) of the composite structure 14 (see FIGS. 1C, 2C, 3C, 4C, 8, 13). The removable chromatic witness assembly 10 (see FIGS. 1A-6) comprising a removable chromatic witness applique 12 (see FIGS. 1A-6) may be formed in rolls, such as in a tape form, or another suitable form.

Figure 8:
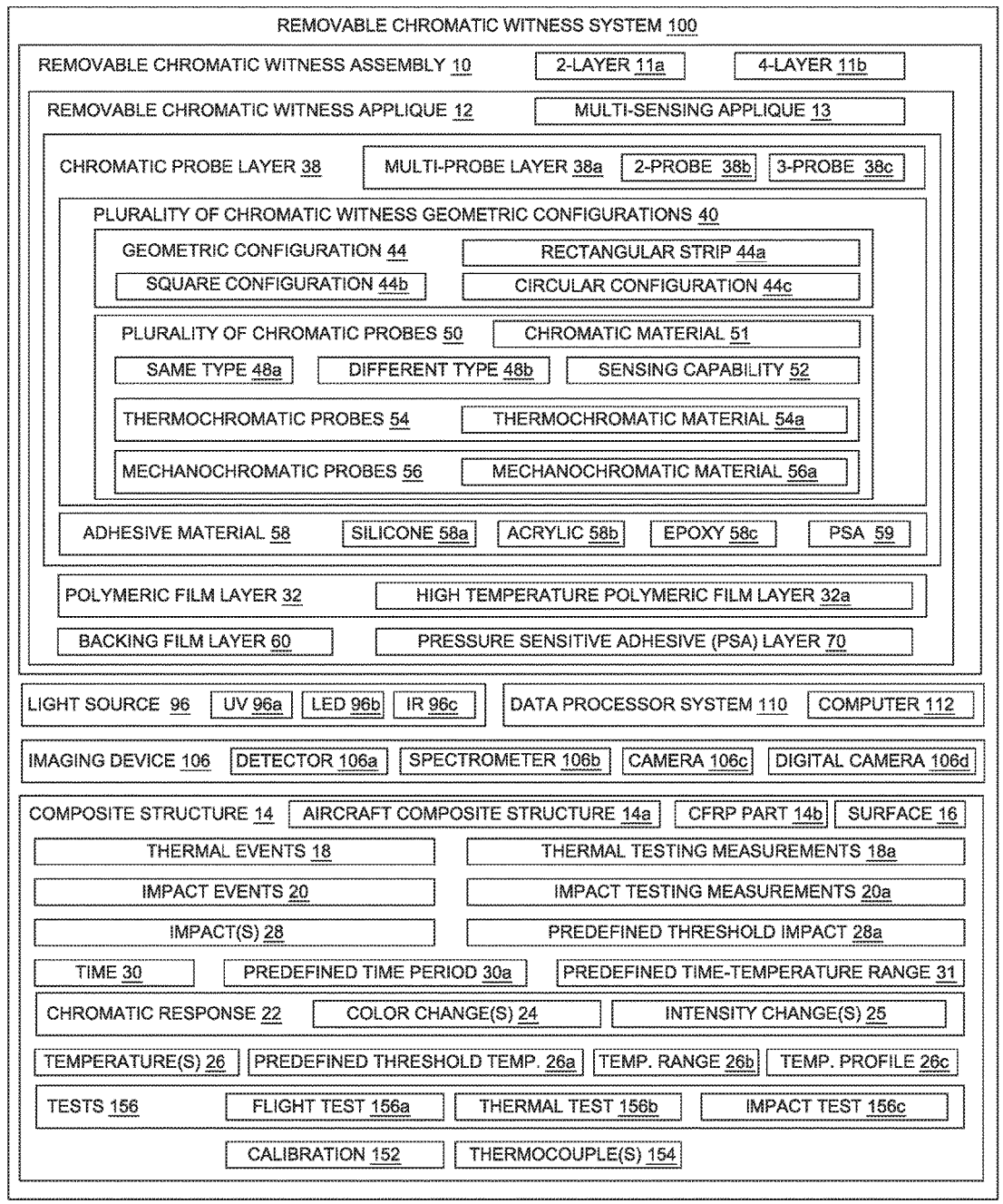
FIG. 8 is an illustration of a functional block diagram showing exemplary embodiments of a removable chromatic witness system of the disclosure.
Figure 9:
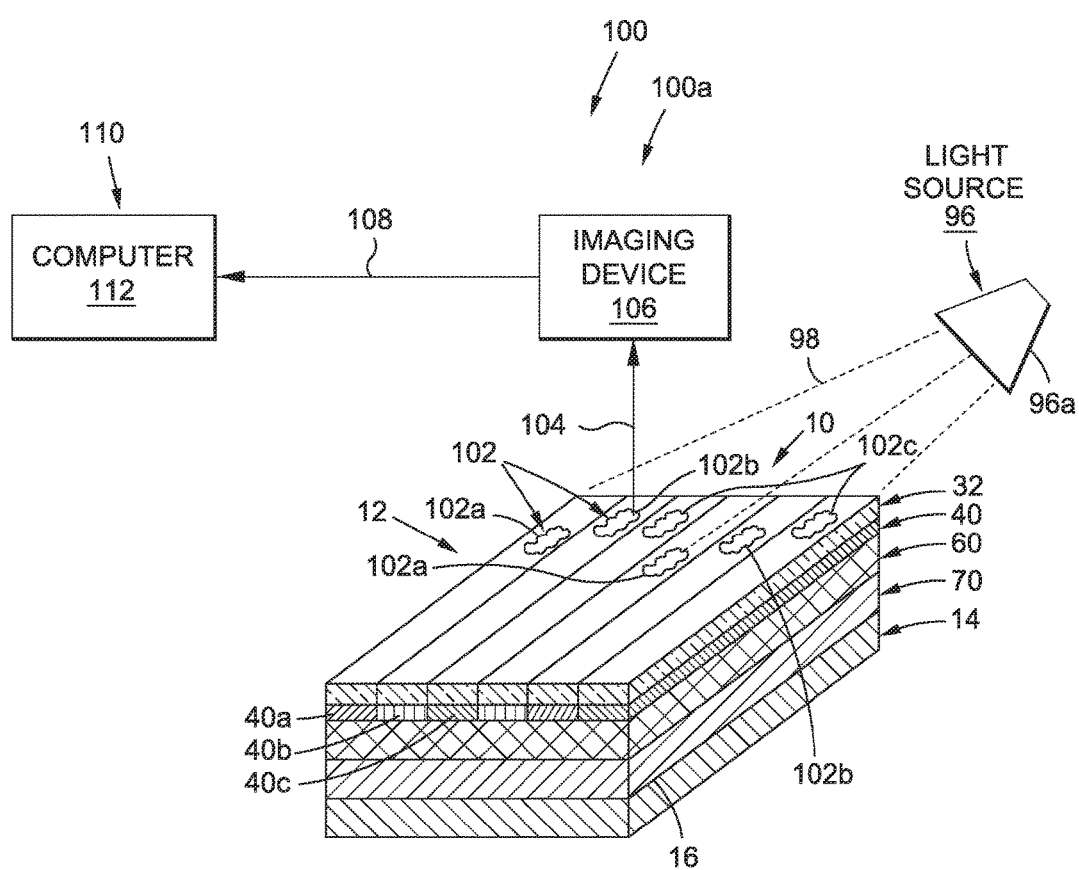
FIG. 9 is a schematic representation of an embodiment of a removable chromatic witness system of the disclosure.
Figure 10:
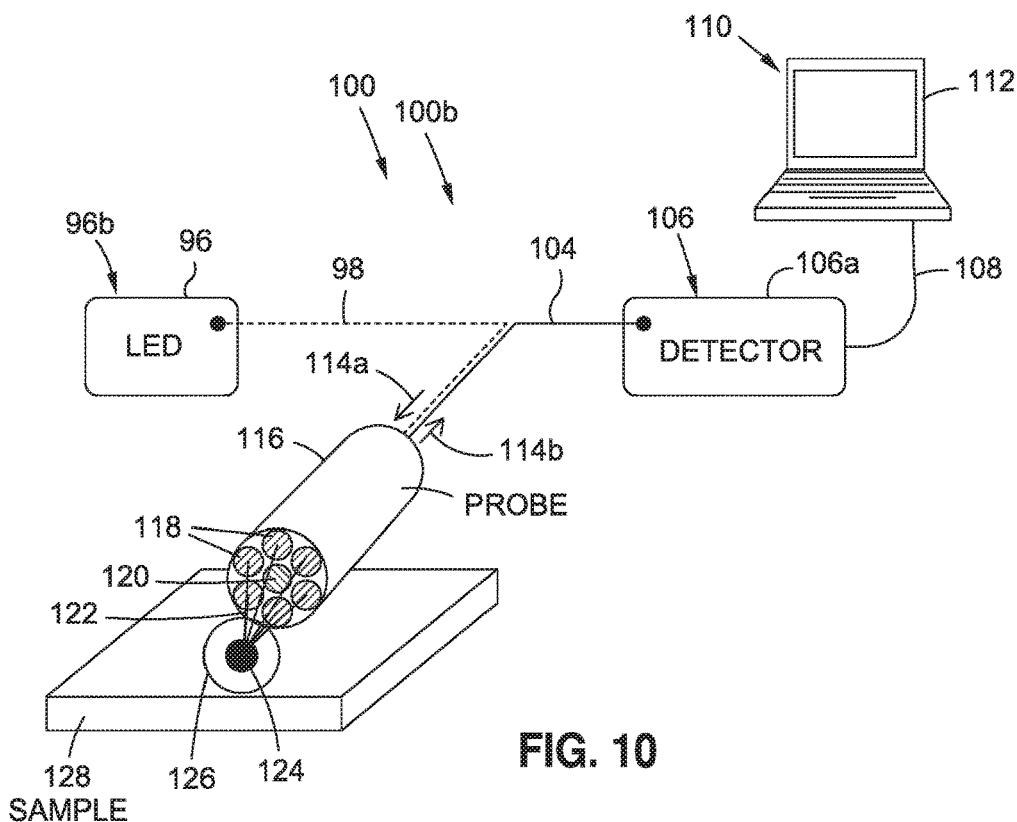
FIG. 10 is a schematic representation of another embodiment of a removable chromatic witness system of the disclosure.

FIGS. 8-10 show exemplary embodiments of a removable chromatic witness system 100 of the disclosure that incorporate embodiments of the removable chromatic witness assembly 10 (see FIGS. 1A-6). In another embodiment, there is provided the removable chromatic witness system 100 (see FIGS. 8-10) to monitor thermal events 18 (see FIG. 8) and impact events 20 (see FIG. 8) on the surface 16 (see FIGS. 8, 9) of the composite structure 14 (see FIGS. 8, 9).

Now referring to FIG. 1A, FIG. 1A is a schematic illustration of a cross-sectional perspective view of an embodiment of a removable chromatic witness assembly 10, such as in the form of removable chromatic witness assembly 10a. As shown in FIG. 1A, the removable chromatic witness assembly 10, such as in the form of removable chromatic witness assembly 10a, comprises a removable chromatic witness applique 12, such as in the form of removable chromatic witness applique 12a.

Figure 1B:
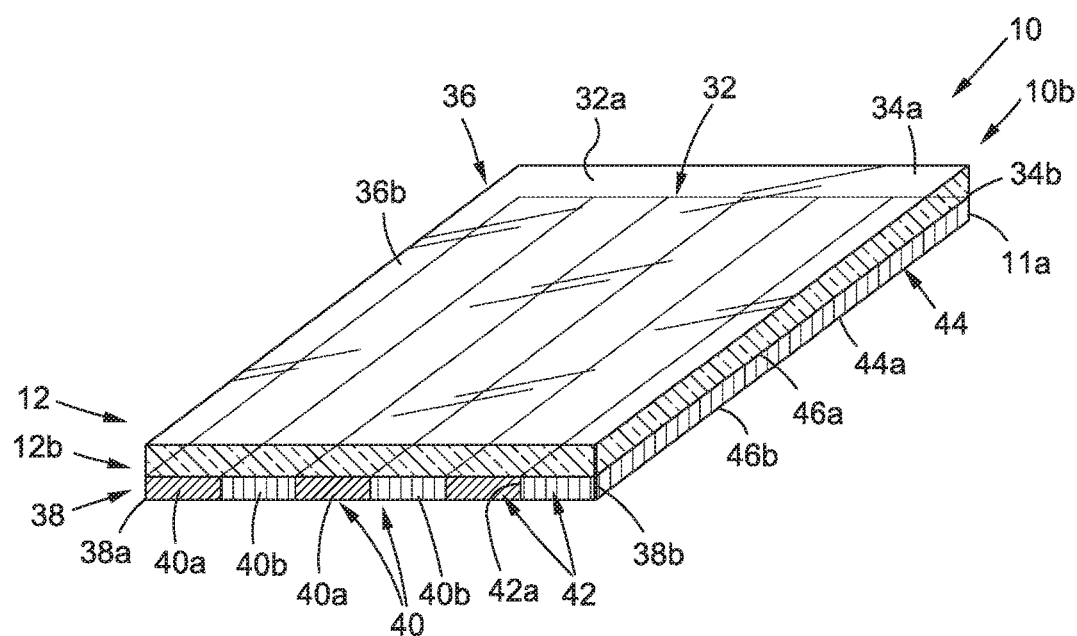
FIG. 1B is a schematic illustration of a cross-sectional perspective view of another embodiment of a removable chromatic witness assembly of the disclosure.

Now referring to FIG. 1B, FIG. 1B is a schematic illustration of a cross-sectional perspective view of another embodiment of a removable chromatic witness assembly 10, such as in the form of removable chromatic witness assembly 10b. As shown in FIG. 1B, the removable chromatic witness assembly 10, such as in the form of removable chromatic witness assembly 10b, comprises a removable chromatic witness applique 12, such as in the form of removable chromatic witness applique 12b.

As shown in FIGS. 1A-1B, the removable chromatic witness assembly 10 comprises a 2-layer removable chromatic witness assembly 11a. The 2-layer removable chromatic witness assembly 11a (see FIGS. 1A-1B) comprises a polymeric film layer 32 (see FIGS. 1A-1B) coupled to a chromatic probe layer 38 (see FIGS. 1A-1B).

The polymeric film layer 32 (see FIGS. 1A-1B) preferably comprises a high temperature polymeric film layer 32a (see FIGS. 1A-1B), such as ethylene tetrafluoroethylene (ETFE) film, or another suitable polymeric film. Preferably, the polymeric film layer 32 (see FIGS. 1A-1B) is stable in a temperature range of between about 130° F. (one hundred thirty degrees Fahrenheit) to about 500° F. (five hundred degrees Fahrenheit). Preferably, the polymeric film layer 32 (see FIGS. 1A-1B) is optically transparent.

As shown in FIGS. 1A-1B, the polymeric film layer 32 has a first side 34*a* and a second side 34*b*, and comprises one or more portions 36. In one embodiment, as shown in FIG. 1A, the removable chromatic witness assembly 10, such as in the form of removable chromatic witness assembly 10*a*, comprises the polymeric film layer 32 segmented, cut, or slit into multiple portions 36*a*. This embodiment may enable ease of maintenance of individual segments or strips, may enable ease of offline analysis of given individual segments or strips, and may enable improved installation of the removable chromatic witness applique 12 (see FIGS. 1A-6) onto contoured surfaces without wrinkling or buckling.

In another embodiment, as shown in FIG. 1B, the removable chromatic witness assembly 10, such as in the form of removable chromatic witness assembly 10*b*, comprises the polymeric film layer 32 as a single portion 36*b*. This embodiment may enable ease of manufacturing, if it is not desired that the polymeric film layer 32 not be cut or segmented into multiple portions 36*a* (see FIG. 1A) but instead be maintained as a single portion 36*b*.

As shown in FIGS. 1A-1B, the chromatic probe layer 38 comprises a multi-probe layer 38*a*, for example, in the form of a 2-probe layer 38*b*. The chromatic probe layer 38 (see FIGS. 1A-1B) of the removable chromatic witness assembly 10 (see FIGS. 1A-1B) comprises a plurality of chromatic witness geometric configurations 40 (see FIGS. 1A-1B) separately coupled in an arrangement 42 (see FIGS. 1A-1B), such as an adjacent repeating arrangement 42*a* (see FIGS. 1A-1B), to the one or more portions 36 (see FIGS. 1A-1B) of the polymeric film layer 32 (see FIGS. 1A-1B).

Figure 7:
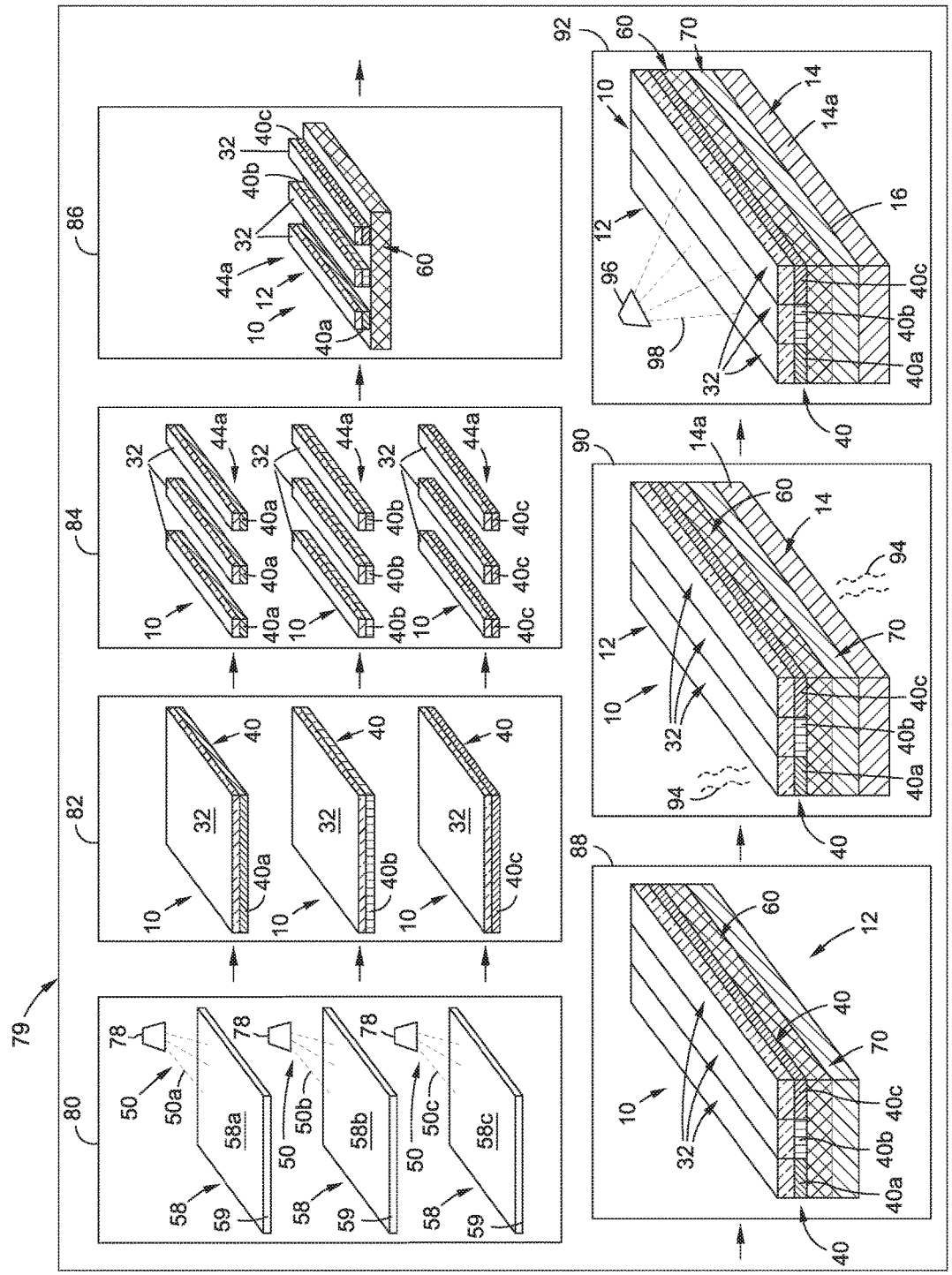
FIG. 7 is a schematic flowchart showing a method of making an embodiment of a removable chromatic witness assembly of the disclosure.

Each chromatic witness geometric configuration 40 (see FIGS. 1A-1B, 7, 8) comprises a plurality of chromatic probes 50 (see FIGS. 7, 8) of a same type 48*a* (see FIG. 8) incorporated into an adhesive material 58 (see FIGS. 7, 8). At least two of each of the plurality of chromatic witness geometric configurations 40 (see FIGS. 1A-1B, 7, 8) have a different type 48*b* (see FIG. 8) of chromatic probe 50 (see FIGS. 7, 8) with a different sensing capability 52 (see FIG. 8) for one of, the thermal events 18 (see FIG. 8) and the impact events 20 (see FIG. 8), on the surface 16 (see FIG. 8) of the composite structure 14 (see FIG. 8). Each different type 48*b* (see FIG. 8) of chromatic probe 50 (see FIGS. 7, 8) in each separate chromatic witness geometric configuration 40 preferably has a different predefined time-temperature range 31 (see FIG. 8), in which the chromatic probe 50 is configured to activate or fluoresce in response to illumination with a light source 94 (see FIGS. 8-10), discussed in further detail below.

As shown in FIGS. 1A-1B, each chromatic witness geometric configuration 40 has a geometric configuration 44, such as in the form of a rectangular strip 44*a*, and each chromatic witness geometric configuration 40 has a first side 46*a* and a second side 46*b*. The geometric configuration 44 (see FIGS. 1A-1B, 8) of each chromatic witness may comprise one of, the rectangular strip 44*a*, a square configuration 44*b* (see FIGS. 6, 8), or any number of other suitable geometric shape configurations 44 (see FIG. 8).

The plurality of chromatic witness geometric configurations 40 (see FIG. 1A) preferably comprise repeating chromatic witness geometric configurations 40*d* (see FIG. 1A). In one embodiment, as shown in FIG. 1A, the repeating chromatic witness geometric configurations 40*d* comprise two repeating chromatic witness geometric configurations 40*d* of a first probe type 40*a* and a second probe type 40*b*, where each of the first probe type 40*a* and the second probe type 40*b* have different types 48*b* (see FIG. 8) of chromatic probes 50 (see FIG. 8).

The plurality of chromatic probes 50 (see FIGS. 7, 8) in each chromatic witness geometric configuration 40 (see FIGS. 1A-1B, 7, 8) are comprised of a chromatic material 51 (see FIG. 8). The chromatic material 51 (see FIG. 8) may comprise chromatic probes 50 or fluorescent dye molecules tailored to activate at a predefined threshold temperature 26*a* (see FIG. 8), a predefined threshold impact 28*a* (see FIG. 8), and/or in a predefined time-temperature range 31. The chromatic probes 50 (see FIGS. 7, 8) may comprise thermochromatic probes 54 (see FIG. 8) comprised of a thermochromatic material 54*a* (see FIG. 8) and tailored to take thermal testing measurements 18*a* (see FIG. 8) of thermal events 18 (see FIG. 8), such as temperatures 26 (see FIG. 8) that exceed predefined threshold temperatures 26*a* (see FIG. 8). The chromatic probes 50 (see FIGS. 7, 8) may further comprise mechanochromatic probes 56 (see FIG. 8) comprised of a mechanochromatic material 56*a* (see FIG. 8) and tailored to take impact testing measurements 20*a* (see FIG. 8) of impact events 20 (see FIG. 8), such as impacts 28 (see FIG. 8) to the composite structure 14 (see FIG. 8). Embodiments of the plurality of chromatic witness geometric configurations 40 (see FIGS. 1A-8) disclosed herein may include fluorescent dye molecules, such as those disclosed in U.S. Pat. No. 8,720,278, to Toivola et al., entitled "Method of Detecting Inconsistencies in Composite Structures and Stress Sensitive Coatings Used Therein," which is incorporated herein by reference in its entirety.

When the thermochromatic probes 54 (see FIG. 8) or thermochromatic material 54*a* (see FIG. 8) are activated by exposure to temperatures 26 (see FIG. 8) that exceed predefined threshold temperatures 26*a* (see FIG. 8) to which they have been tailored, such as temperatures 26 (see FIG. 8) that are very high and that may cause thermal damage, the thermochromatic probes 54 (see FIG. 8) or thermochromatic material 54*a* (see FIG. 8) undergo fluorescent shifts and emit fluorescence emissions 126 (see FIG. 10). When illuminated by a light source 94 (see FIGS. 8-10), discussed in further detail below, of a suitable wavelength, the fluorescent shifts in the thermochromatic probes 54 (see FIG. 8) or thermochromatic material 54*a* (see FIG. 8) become visible, manifesting themselves as fluorescence emissions 126 (see FIG. 10), such as in the form of color changes 24 (see FIG. 8) and intensity changes 25 (see FIG. 8) in the colors.

Similarly, when the mechanochromatic probes 56 (see FIG. 8) or mechanochromatic material 56*a* (see FIG. 8) are activated by experiencing impacts 28 (see FIG. 8) that exceed predefined threshold impacts 28*a* (see FIG. 8) to which they have been tailored, such as impacts 28 (see FIG. 8) of a specific force, the mechanochromatic probes 56 (see FIG. 8) or mechanochromatic material 56*a* (see FIG. 8) undergo fluorescent shifts and emit fluorescence emissions 126 (see FIG. 10). When illuminated by a light source 94 (see FIGS. 8-10), discussed in further detail below, of a suitable wavelength, the fluorescent shifts in the mechanochromatic probes 56 (see FIG. 8) or mechanochromatic material 56*a* (see FIG. 8) become visible, manifesting themselves as fluorescence emissions 126 (see FIG. 10), such as in the form of color changes 24 (see FIG. 8) and intensity changes 25 (see FIG. 8) in the colors. Thus, the mechanochromatic probes 56 (see FIG. 8) change color (absorbance and emission) in response to mechanical force.

In fabricating the plurality of chromatic witness geometric configurations 40 (see FIGS. 1A-8), the plurality of chromatic probes 50 (see FIGS. 7, 8) are added and incorporated into an adhesive material 58 (see FIGS. 7, 8). The adhesive material 58 (see FIGS. 7, 8) may comprise one or more of a silicone adhesive 58a (see FIGS. 7, 8), an acrylic adhesive 58b (see FIGS. 7, 8), an epoxy adhesive 58c (see FIGS. 7, 8), or another suitable adhesive material 58 (see FIGS. 7, 8). Preferably, the adhesive material 58 (see FIGS. 7, 8) is a pressure sensitive adhesive (PSA) 59 (see FIGS. 7, 8). Each chromatic witness geometric configuration 40 that forms the chromatic probe layer 38 preferably has a thickness of from about 0.001 inch to about 0.002 inch. However, other suitable thicknesses may be used.

Figure 1C:
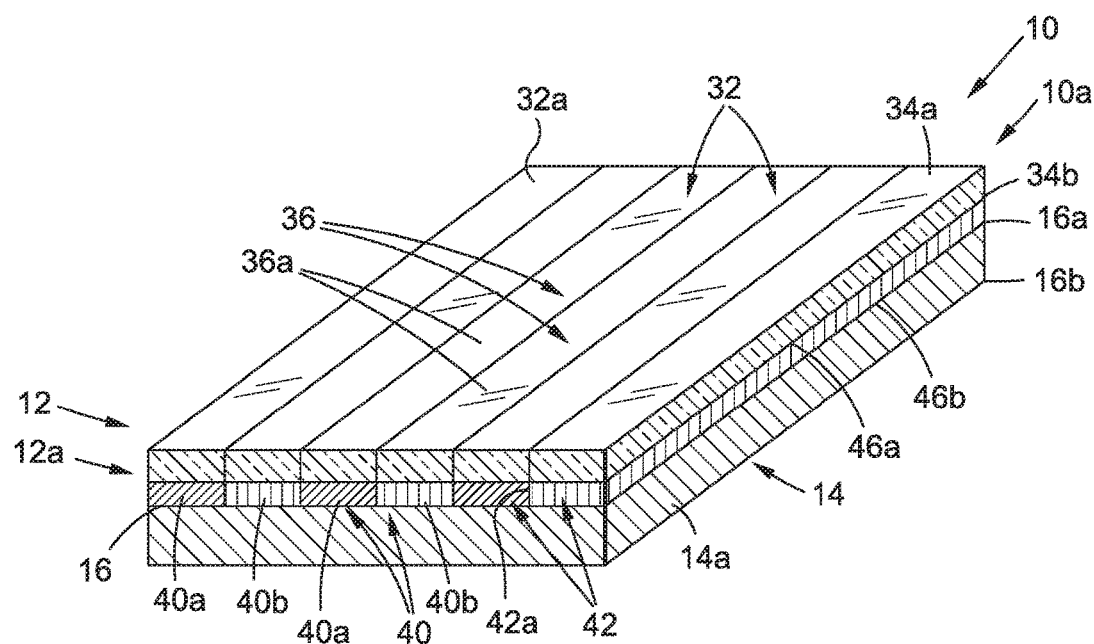
FIG. 1C is a schematic illustration of a cross-sectional perspective view of the removable chromatic witness assembly of FIG. 1A coupled to a composite structure.
Figure 1D:
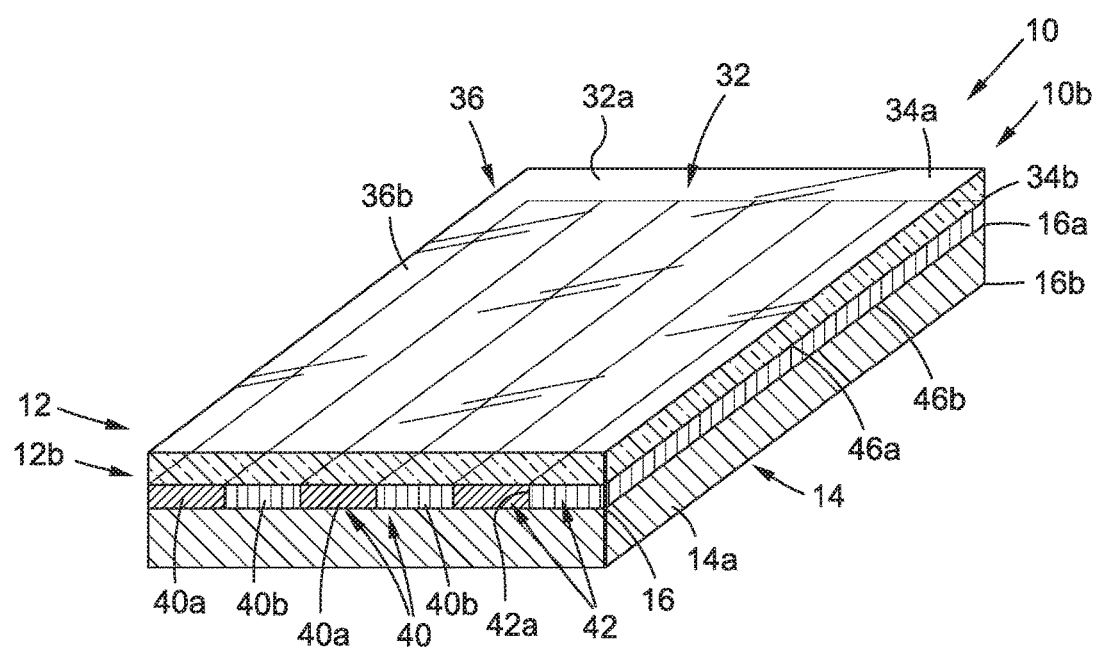
FIG. 1D is a schematic illustration of a cross-sectional perspective view of the removable chromatic witness assembly of FIG. 1B coupled to a composite structure.

Now referring to FIGS. 1C-1D, FIG. 1C is a schematic illustration of a cross-sectional perspective view of the removable chromatic witness assembly 10, such as in the form of removable chromatic witness assembly 10a, of FIG. 1A, coupled to a surface 16 of a composite structure 14, such as in the form of an aircraft composite structure 14a. FIG. 1D is a schematic illustration of a cross-sectional perspective view of the removable chromatic witness assembly 10, such as in the form of removable chromatic witness assembly 10b, of FIG. 1B, coupled to the surface 16 of the composite structure 14, such as in the form of the aircraft composite structure 14a.

As shown in FIGS. 1C-1D, the composite structure 14 has a first side 16a and a second side 16b, and the second side 46b of each chromatic witness geometric configuration 40 is adjacent the surface 16 of the composite structure 14. The removable chromatic witness assembly 10 (see FIGS. 1C-1D) in the form of the removable chromatic witness applique 12 (see FIGS. 1C-1D) is configured to be removably applied directly and continuously to the surface 16 (see FIGS. 1C-1D) of the composite structure 14 (see FIGS. 1C-1D), and configured to monitor the thermal events 18 (see FIG. 8) and the impact events 20 (see FIG. 8) on the surface 16 (see FIGS. 1C-1D) of the composite structure 14 (see FIGS. 1C-1D). The removable chromatic witness applique 12 (see FIGS. 1C-1D) is preferably a multi-sensing applique 13 (see FIG. 8) configured to take thermal testing measurements 18a (see FIG. 8) and impact testing measurements 20a (see FIG. 8) across the surface 16 (see FIGS. 1C-1D) of the composite structure 14 (see FIGS. 1C-1D) over which the removable chromatic witness applique 12 (see FIGS. 1C-1D) is applied.

Figure 2A:
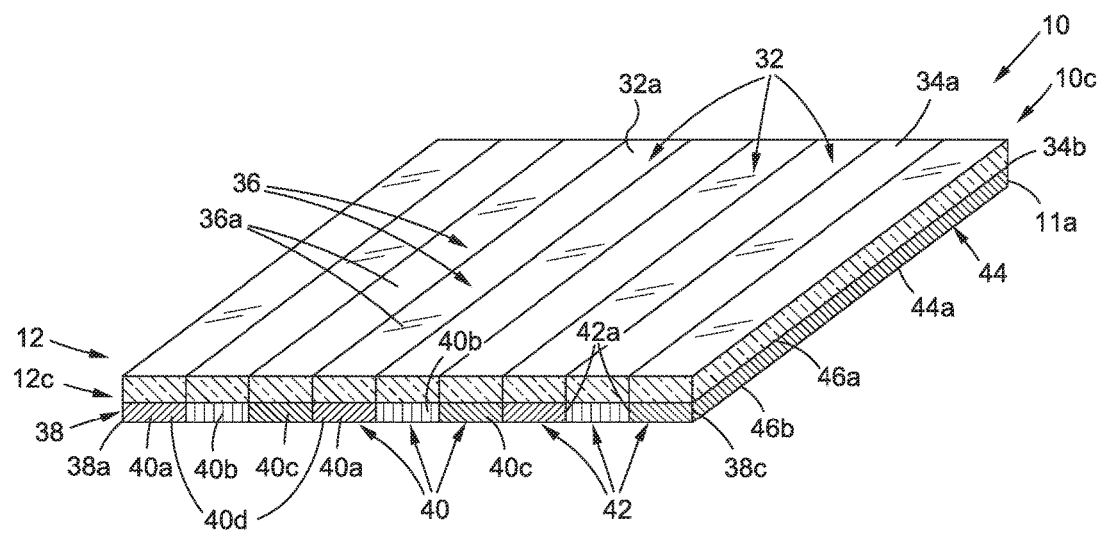
FIG. 2A is a schematic illustration of a cross-sectional perspective view of yet another embodiment of a removable chromatic witness assembly of the disclosure.
Figure 2B:
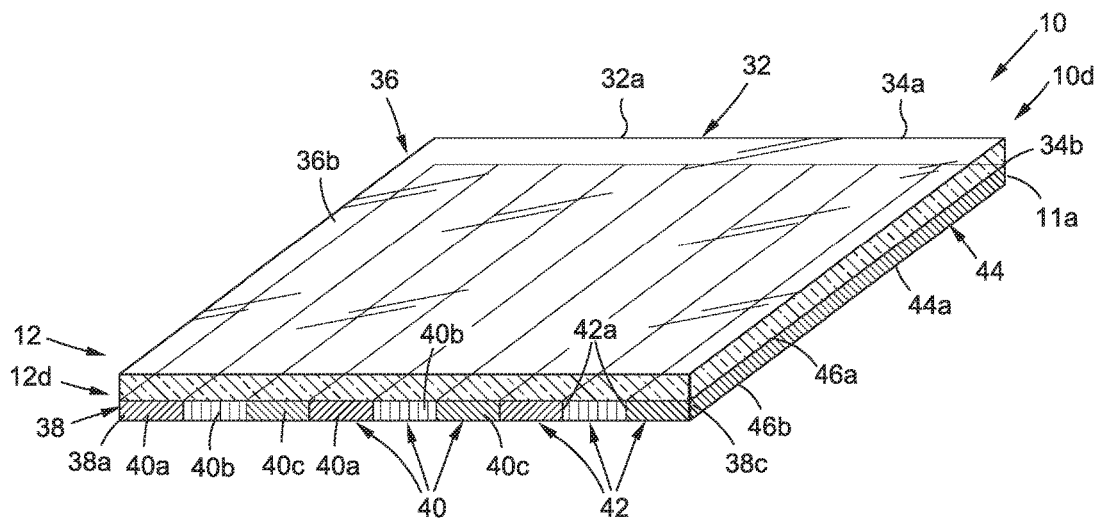
FIG. 2B is a schematic illustration of a cross-sectional perspective view of yet another embodiment of a removable chromatic witness assembly of the disclosure.

Now referring to FIGS. 2A-2D, FIGS. 2A-2D show embodiments of the removable chromatic witness assembly 10 identical to the embodiments shown in FIGS. 1A-1D, except that the chromatic probe layer 38 (see FIGS. 2A-2B) comprises a multi-probe layer 38a (see FIGS. 2A-2B) in the form of a 3-probe layer 38b in a repeating arrangement (see FIGS. 2A-2B). While a 2-probe layer 38a (see FIG. 1A) and a 3-probe layer 38b (see FIG. 2A) are shown, any number of chromatic probes 50 in a repeating arrangement, such as more that three (3) different types 48b (see FIG. 8) of chromatic probes 50 (see FIG. 8), may be used to take measurements on the surface 16 (see FIGS. 1C, 2C) of the composite structure 14 (see FIGS. 1C, 2C) over which the removable chromatic witness assembly 10 (see FIGS. 1C, 2C) comprising the removable chromatic witness applique 12 (see FIGS. 1C, 2C) is applied.

Now referring to FIG. 2A, FIG. 2A is a schematic illustration of a cross-sectional perspective view of another embodiment of the removable chromatic witness assembly 10, such as in the form of removable chromatic witness assembly 10c, of the disclosure. As shown in FIG. 2A, the removable chromatic witness assembly 10, such as in the form of removable chromatic witness assembly 10c, comprises a removable chromatic witness applique 12, such as in the form of removable chromatic witness applique 12c.

Now referring to FIG. 2B, FIG. 2B is a schematic illustration of a cross-sectional perspective view of another embodiment of a removable chromatic witness assembly 10, such as in the form of removable chromatic witness assembly 10d, of the disclosure. As shown in FIG. 2B, the removable chromatic witness assembly 10, such as in the form of removable chromatic witness assembly 10d, comprises a removable chromatic witness applique 12, such as in the form of removable chromatic witness applique 12d.

Similar to FIGS. 1A-1B, the removable chromatic witness assembly 10 shown in FIGS. 2A-2B comprises a 2-layer removable chromatic witness assembly 11a comprising the polymeric film layer 32, such as a high temperature polymeric film layer 32a, having the first side 34a, the second side 34b, and portions 36, including multiple portions 36a (see FIG. 2A) or a single portion 36b (see FIG. 2B). The polymeric film layer 32 (see FIGS. 2A-2B) is coupled to the chromatic probe layer 38 (see FIGS. 2A-2B) comprised of the plurality of chromatic witness geometric configurations 40 (see FIGS. 2A-2B) separately coupled in an arrangement 42 (see FIGS. 2A-2B), such as adjacent repeating arrangement 42a (see FIGS. 2A-2B), to the one or more portions 36 (see FIGS. 2A-2B) of the polymeric film layer 32 (see FIGS. 2A-2B).

As shown in FIGS. 2A-2B, each chromatic witness geometric configuration 40 has the geometric configuration 44, such as in the form of rectangular strip 44a, and each chromatic witness geometric configuration 40 has the first side 46a and the second side 46b. The plurality of chromatic witness geometric configurations 40 (see FIG. 2A) preferably comprise repeating chromatic witness geometric configurations 40d (see FIG. 2A) in the form of three repeating chromatic witness geometric configurations 40d of a first probe type 40a, a second probe type 40b, and a third probe type 40c, where each of the first probe type 40a, the second probe type 40b, and the third probe type 40c, have different types 48b (see FIG. 8) of chromatic probes 50 (see FIG. 8). In fabricating the plurality of chromatic witness geometric configurations 40 (see FIGS. 2A-2B), the plurality of chromatic probes 50 (see FIGS. 7, 8) are added and incorporated into the adhesive material 58 (see FIGS. 7, 8), as discussed above.

Figure 2C:
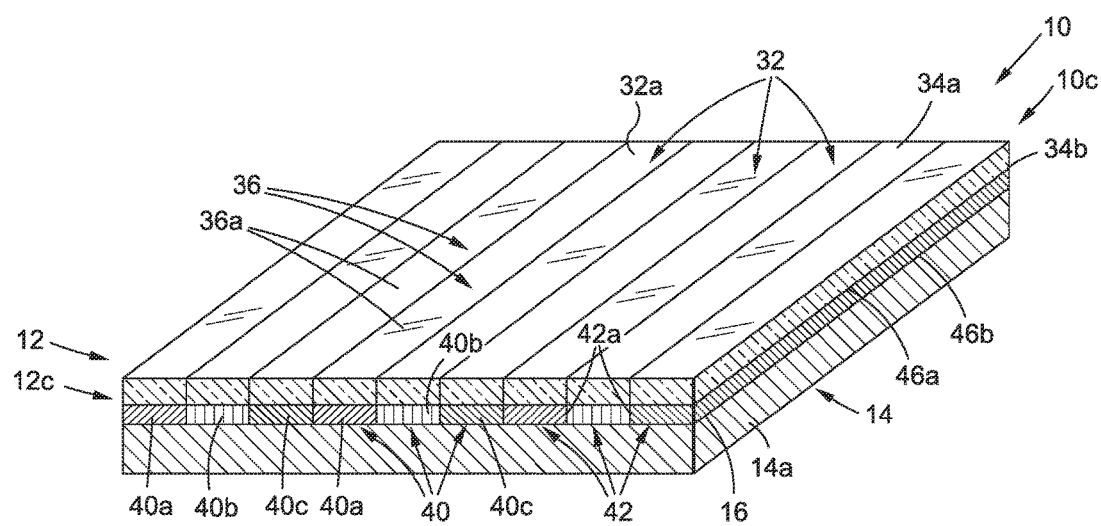
FIG. 2C is a schematic illustration of a cross-sectional perspective view of the removable chromatic witness assembly of FIG. 2A coupled to a composite structure.
Figure 2D:
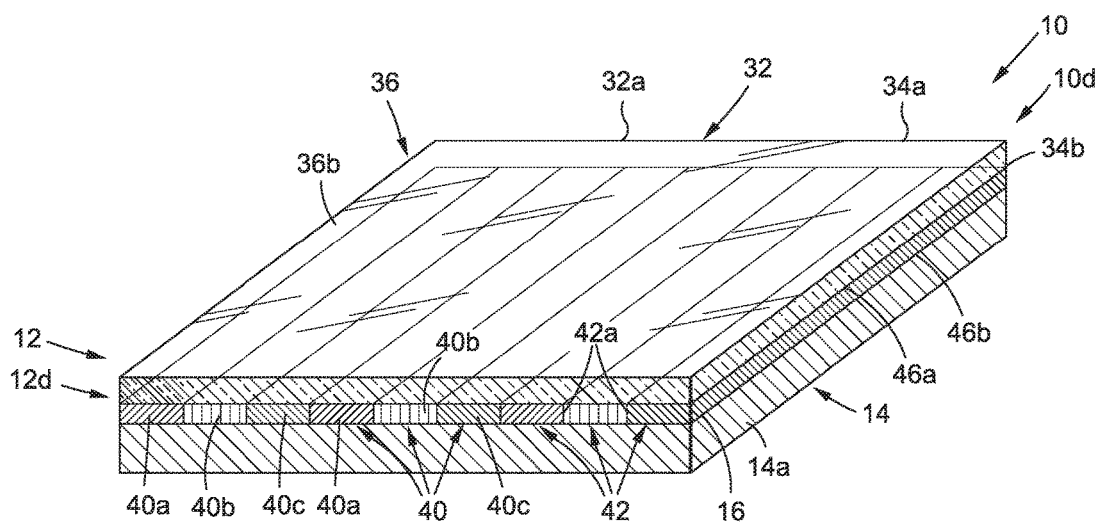
FIG. 2D is a schematic illustration of a cross-sectional perspective view of the removable chromatic witness assembly of FIG. 2B coupled to a composite structure.

Now referring to FIGS. 2C-2D, FIG. 2C is a schematic illustration of a cross-sectional perspective view of the removable chromatic witness assembly 10, such as in the form of removable chromatic witness assembly 10c, of FIG. 2A, coupled to the surface 16 of the composite structure 14, such as in the form of aircraft composite structure 14a. FIG. 2D is a schematic illustration of a cross-sectional perspective view of the removable chromatic witness assembly 10, such as in the form of removable chromatic witness assembly 10d, of FIG. 2B, coupled to the surface 16 of the composite structure 14, such as in the form of aircraft composite structure 14a. The removable chromatic witness assembly 10 (see FIGS. 2C-2D) in the form of the removable chromatic witness applique 12 (see FIGS. 2C-2D) is configured to be removably applied directly and continuously to the surface 16 (see FIGS. 2C-2D) of the composite structure 14 (see FIGS. 2C-2D), and configured to monitor the thermal events 18 (see FIG. 8) and the impact events 20 (see FIG. 8) on the surface 16 (see FIGS. 2C-2D) of the composite structure 14 (see FIGS. 2C-2D).

Figure 3A:
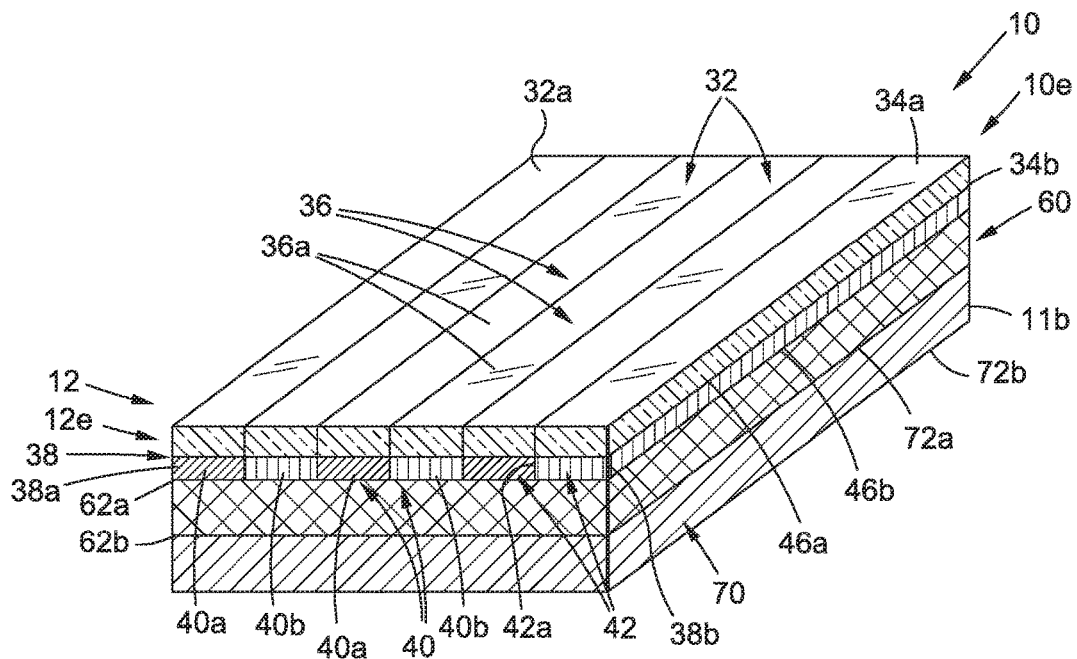
FIG. 3A is a schematic illustration of a cross-sectional perspective view of yet another embodiment of a removable chromatic witness assembly of the disclosure.
Figure 3B:
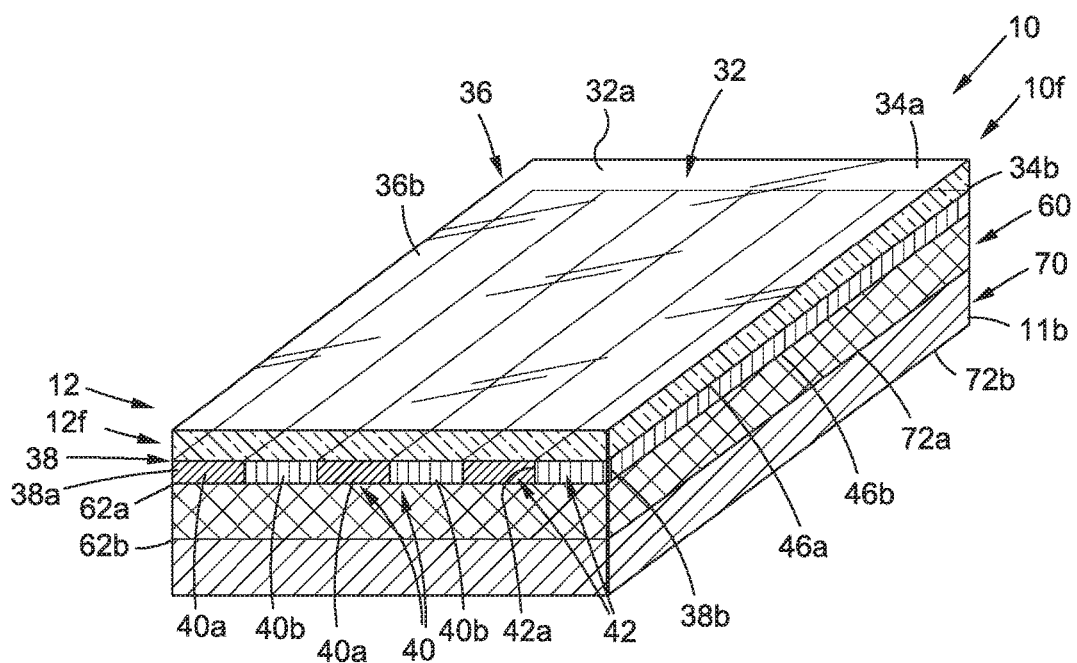
FIG. 3B is a schematic illustration of a cross-sectional perspective view of yet another embodiment of a removable chromatic witness assembly of the disclosure.

Now referring to FIGS. 3A-3B, FIGS. 3A-3B show embodiments of the removable chromatic witness assembly 10 identical to the embodiments shown in FIGS. 1A-1B, except that the removable chromatic witness assembly 10 shown in FIGS. 3A-3B comprises a 4-layer removable chromatic witness assembly 11b comprising the polymeric film layer 32 coupled to the chromatic probe layer 38, and comprising an additional backing film layer 60 and an additional pressure sensitive adhesive (PSA) layer 70. The backing film layer 60 (see FIGS. 3A-3B) is coupled to the plurality of chromatic witness geometric configurations 40 (see FIGS. 3A-3B) of the chromatic probe layer 38 (see FIGS. 3A-3B). The pressure sensitive adhesive (PSA) layer 70 (see FIGS. 3A-3B) is coupled to the backing film layer 60 (see FIGS. 3A-3B).

Now referring to FIG. 3A, FIG. 3A is a schematic illustration of a cross-sectional perspective view of another embodiment of the removable chromatic witness assembly 10, such as in the form of removable chromatic witness assembly 10e, of the disclosure. As shown in FIG. 3A, the removable chromatic witness assembly 10, such as in the form of removable chromatic witness assembly 10e, comprises a removable chromatic witness applique 12, such as in the form of removable chromatic witness applique 12e.

Now referring to FIG. 3B, FIG. 3B is a schematic illustration of a cross-sectional perspective view of another embodiment of the removable chromatic witness assembly 10, such as in the form of removable chromatic witness assembly 10f, of the disclosure. As shown in FIG. 3B, the removable chromatic witness assembly 10, such as in the form of removable chromatic witness assembly 10f, comprises a removable chromatic witness applique 12, such as in the form of removable chromatic witness applique 12f.

Similar to FIGS. 1A-1B, the removable chromatic witness assembly 10 shown in FIGS. 3A-3B comprises the polymeric film layer 32, such as the high temperature polymeric film layer 32a, having the first side 34a, the second side 34b, and portions 36, including multiple portions 36a (see FIG. 3A) or a single portion 36b (see FIG. 3B), coupled to the chromatic probe layer 38. The chromatic probe layer 38 (see FIGS. 3A-3B) is comprised of the plurality of chromatic witness geometric configurations 40 (see FIGS. 3A-3B) separately coupled in an arrangement 42 (see FIGS. 3A-3B), such as adjacent repeating arrangement 42a (see FIGS. 3A-3B), to the one or more portions 36 (see FIGS. 3A-3B) of the polymeric film layer 32 (see FIGS. 3A-3B).

As shown in FIGS. 3A-3B, the chromatic probe layer 38 comprises the multi-probe layer 38a, for example, in the form of 2-probe layer 38b having each first probe type 40a adjacent to each second probe type 40b. As further shown in FIGS. 3A-3B, each chromatic witness geometric configuration 40 has the geometric configuration 44, such as in the form of rectangular strip 44a, and each chromatic witness geometric configuration 40 has the first side 46a and the second side 46b. In fabricating the plurality of chromatic witness geometric configurations 40 (see FIGS. 3A-3B), the plurality of chromatic probes 50 (see FIGS. 7, 8) are added and incorporated into the adhesive material 58 (see FIGS. 7, 8), as discussed above.

As further shown in FIGS. 3A-3B, the backing film layer 60 has a first side 62a and a second side 62b, and the first side 62 of the backing film layer 60 is coupled to the second side 46b of each of the chromatic witness geometric configuration 40 of the chromatic probe layer 38. The backing film layer 60 (see FIGS. 3A-3B) may comprise the same or similar material as the polymeric film layer (see FIGS. 3A-3B), or may comprise a different material. For example, the backing film layer 60 (see FIGS. 3A-3B), may comprise a high temperature polymeric film layer, such as ethylene tetrafluoroethylene (ETFE) film, or another suitable polymeric film, that is stable in a temperature range of between about 130° F. to about 500° F. Preferably, the backing film layer 60 (see FIGS. 3A-3B) is optically transparent. The backing film layer 60 (see FIGS. 3A-3B) may be dual etched on each of the first side 62a (see FIGS. 3A-3B) and the second side 62b (see FIGS. 3A-3B) to increase the adhesion of the backing film layer 60 (see FIGS. 3A-3B) to the chromatic witness geometric configurations 40 and to the PSA layer 70. The backing film layer 60 (see FIGS. 3A-3B) may have a width of 3 inches, a width of 4 inches, a width of 12 inches, or another suitable width.

As further shown in FIGS. 3A-3B, the pressure sensitive adhesive (PSA) layer 70 has a first side 72a and a second side 72b, and the first side 72a of the PSA layer 70 is coupled to the second side 62b of the backing film layer 60. The PSA layer 70 may comprise a high temperature polymeric film layer, such as a high temperature silicone film, or another suitable high temperature polymeric film, that is stable in a temperature range of between about 130° F. to about 500° F. Preferably, the PSA layer 70 (see FIGS. 3A-3B) is optically transparent.

Figure 3C:
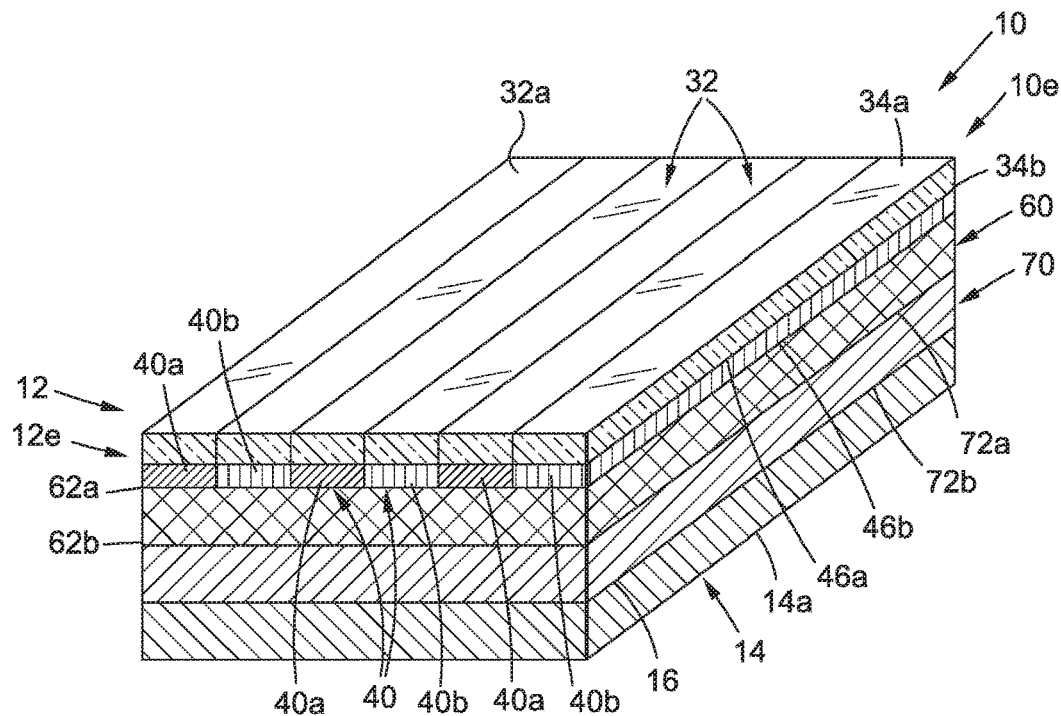
FIG. 3C is a schematic illustration of a cross-sectional perspective view of the removable chromatic witness assembly of FIG. 3A coupled to a composite structure.
Figure 3D:
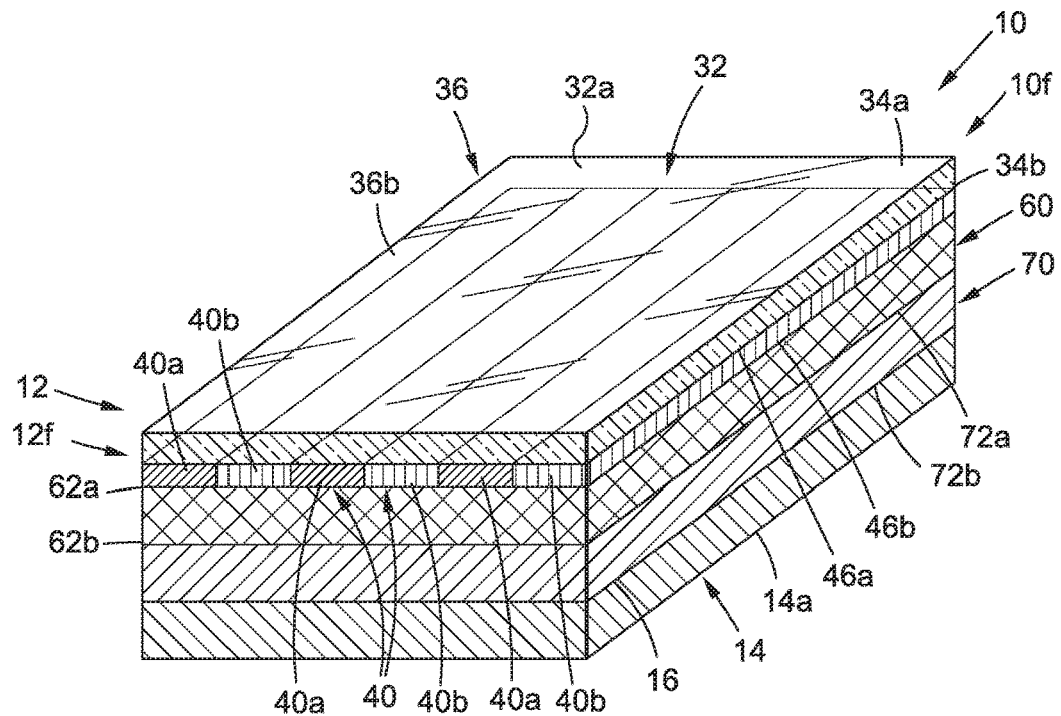
FIG. 3D is a schematic illustration of a cross-sectional perspective view of the removable chromatic witness assembly of FIG. 3B coupled to a composite structure.

Now referring to FIGS. 3C-3D, FIG. 3C is a schematic illustration of a cross-sectional perspective view of the removable chromatic witness assembly 10, such as in the form of removable chromatic witness assembly 10e, of FIG. 3A coupled to the surface 16 of the composite structure 14, such as in the form of aircraft composite structure 14a. FIG. 3D is a schematic illustration of a cross-sectional perspective view of the removable chromatic witness assembly 10, such as in the form of removable chromatic witness assembly 10f, of FIG. 3B coupled to the surface 16 of the composite structure 14, such as in the form of aircraft composite structure 14a. The removable chromatic witness assembly 10 (see FIGS. 3C-3D) in the form of the removable chromatic witness applique 12 (see FIGS. 3C-3D) is configured to be removably applied directly and continuously to the surface 16 (see FIGS. 3C-3D) of the composite structure 14 (see FIGS. 3C-3D), and configured to monitor the thermal events 18 (see FIG. 8) and the impact events 20 (see FIG. 8) on the surface 16 (see FIGS. 3C-3D) of the composite structure 14 (see FIGS. 3C-3D). As shown in FIGS. 3C-3D, the second side 72b of the PSA layer 70 is coupled to the surface 16 of the composite structure 14. The PSA layer 70 enables removability of the removable chromatic witness applique 12, and the backing film layer 60 provides protection of the plurality of chromatic probes 50 in the chromatic witness geometric configuration 40 of the chromatic probe layer 38, and the backing film layer 60 provides ease of handling during removal of the removable chromatic witness applique 12 from the surface 16 of the composite structure 14.

Figure 4A:
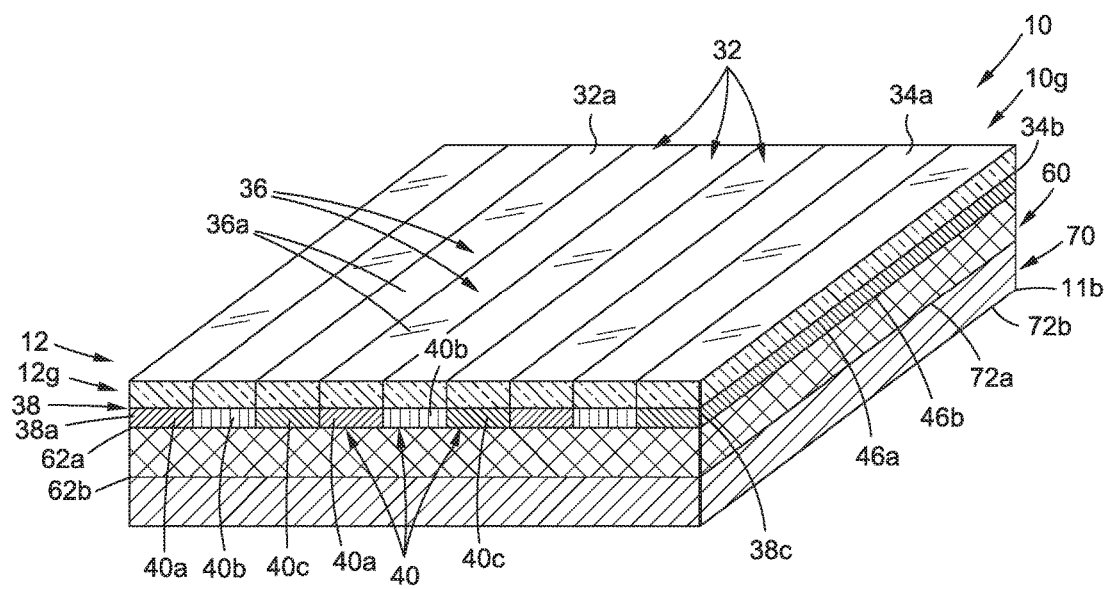
FIG. 4A is a schematic illustration of a cross-sectional perspective view of yet another embodiment of a removable chromatic witness assembly of the disclosure.
Figure 4B:
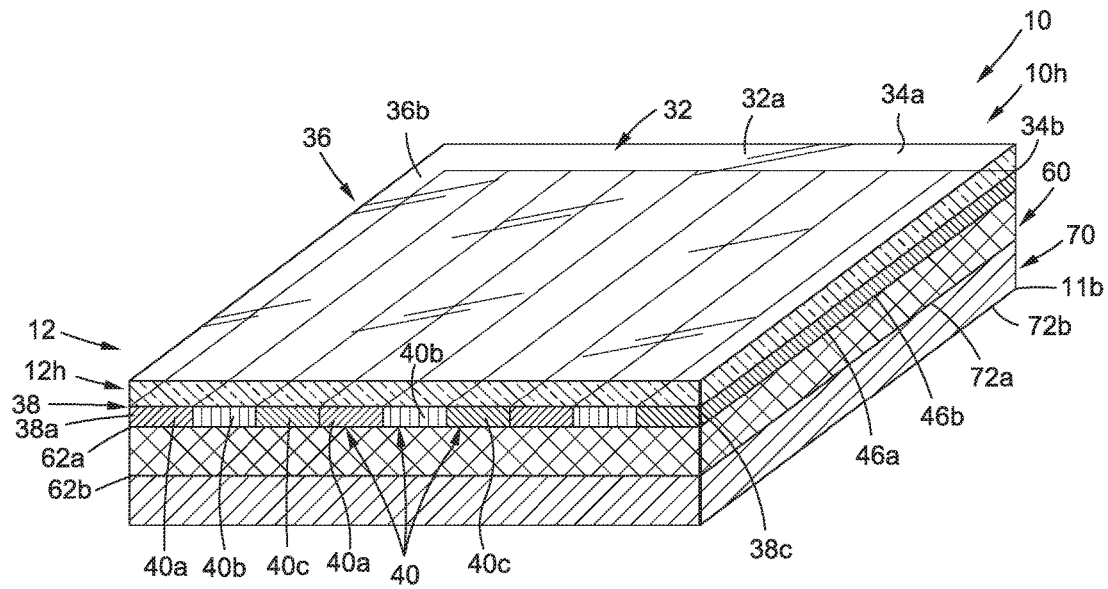
FIG. 4B is a schematic illustration of a cross-sectional perspective view of yet another embodiment of a removable chromatic witness assembly of the disclosure.

Now referring to FIGS. 4A-4D, FIGS. 4A-4D show embodiments of the removable chromatic witness assembly 10 identical to the embodiments shown in FIGS. 3A-3D, except that the chromatic probe layer 38 (see FIGS. 4A-4B) comprises a multi-probe layer 38a (see FIGS. 4A-4B) in the form of a 3-probe layer 38b (see FIGS. 4A-4B).

Now referring to FIG. 4A, FIG. 4A is a schematic illustration of a cross-sectional perspective view of another embodiment of the removable chromatic witness assembly 10, such as in the form of removable chromatic witness assembly 10g, of the disclosure. As shown in FIG. 4A, the removable chromatic witness assembly 10, such as in the form of removable chromatic witness assembly 10g, comprises a removable chromatic witness applique 12, such as in the form of removable chromatic witness applique 12g.

Now referring to FIG. 4B, FIG. 4B is a schematic illustration of a cross-sectional perspective view of another embodiment of a removable chromatic witness assembly 10, such as in the form of removable chromatic witness assembly 10h, of the disclosure. As shown in FIG. 4B, the removable chromatic witness assembly 10, such as in the form of removable chromatic witness assembly 10h, comprises a removable chromatic witness applique 12, such as in the form of removable chromatic witness applique 12h.

Similar to FIGS. 3A-3B, the removable chromatic witness assembly 10 shown in FIGS. 4A-4B comprises a 4-layer removable chromatic witness assembly 11b comprising the polymeric film layer 32, such as a high temperature polymeric film layer 32a, having the first side 34a, the second side 34b, and portions 36, including multiple portions 36a (see FIG. 4A) or a single portion 36b (see FIG. 4B), coupled to the chromatic probe layer 38. The chromatic probe layer 38 (see FIGS. 4A-4B) comprised of the plurality of chromatic witness geometric configurations 40 (see FIGS. 4A-4B) separately coupled in an arrangement 42 (see FIGS. 4A-4B), such as adjacent repeating arrangement 42a (see FIGS. 4A-4B), to the one or more portions 36 of the polymeric film layer 32 (see FIGS. 4A-4B).

Similar to FIGS. 3A-3B, the removable chromatic witness assembly 10 shown in FIGS. 4A-4B further comprises the backing film layer 60, with the first side 602a and the second side 62b, coupled to the plurality of chromatic witness geometric configurations 40 of the chromatic probe layer 38, and coupled to the pressure sensitive adhesive (PSA) layer 70 having the first side 72a and the second side 72b.

As shown in FIGS. 4A-4B, each chromatic witness geometric configuration 40 has the geometric configuration 44, such as in the form of the rectangular strip 44a, and each chromatic witness geometric configuration 40 has the first side 46a and the second side 46b. The plurality of chromatic witness geometric configurations 40 (see FIGS. 4A-4B) comprise the first probe types 40a, the second probe types 40b, and the third probe types 40c, where each of the first probe type 40a, the second probe type 40b, and the third probe type 40c, have different types 48b (see FIG. 8) of chromatic probes 50 (see FIG. 8). In fabricating the plurality of chromatic witness geometric configurations 40 (see FIGS. 4A-4B), the plurality of chromatic probes 50 (see FIGS. 7, 8) are added and incorporated into the adhesive material 58 (see FIGS. 7, 8), as discussed above.

Figure 4C:
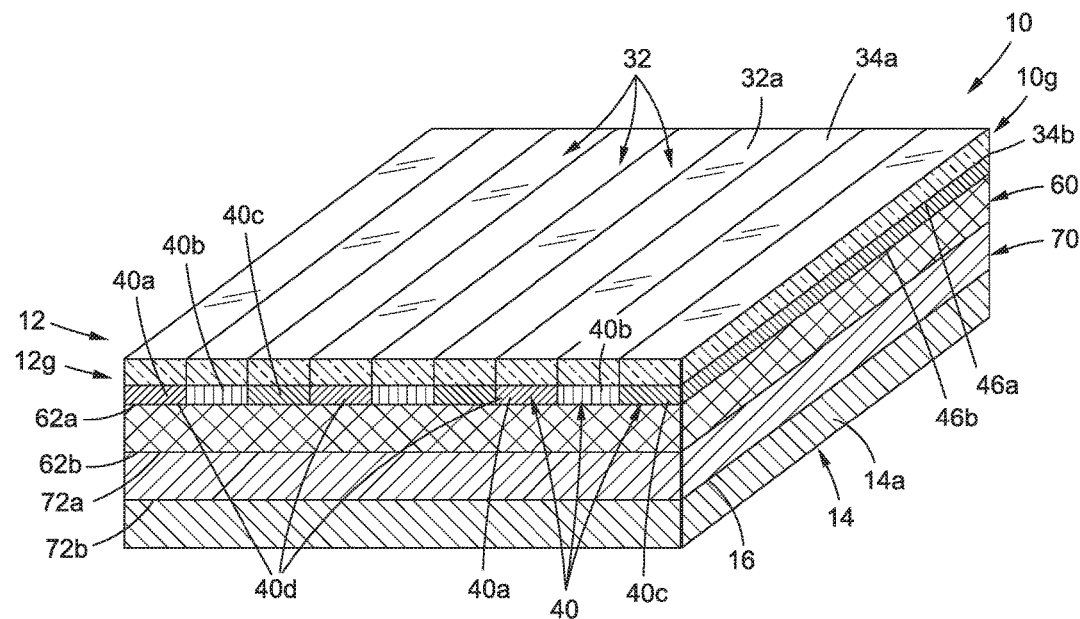
FIG. 4C is a schematic illustration of a cross-sectional perspective view of the removable chromatic witness assembly of FIG. 4A coupled to a composite structure.
Figure 4D:
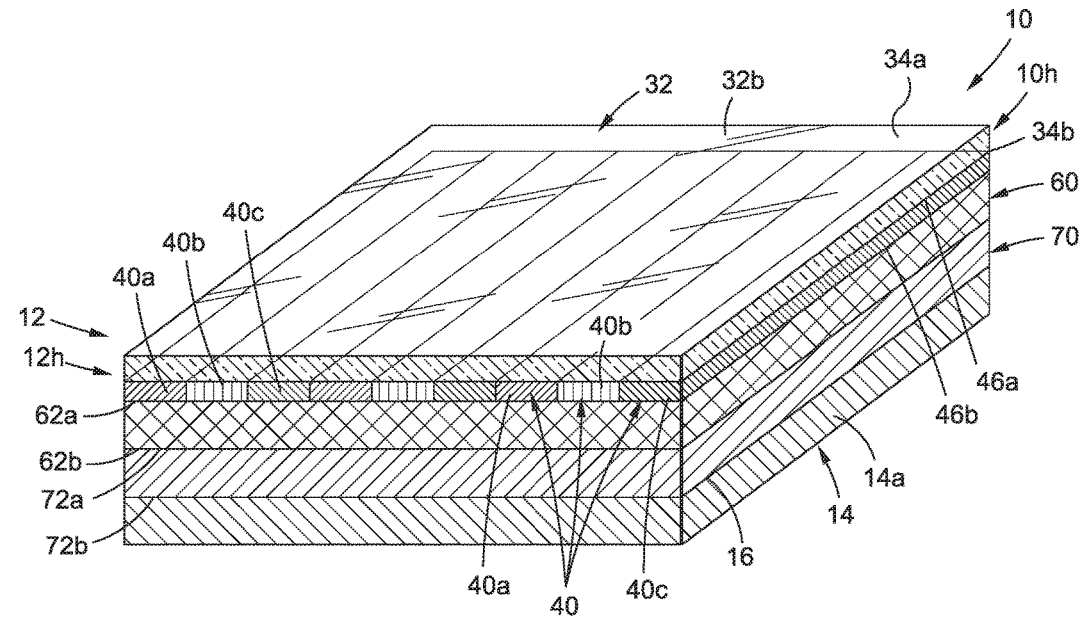
FIG. 4D is a schematic illustration of a cross-sectional perspective view of the removable chromatic witness assembly of FIG. 4B coupled to a composite structure.

Now referring to FIGS. 4C-4D, FIG. 4C is a schematic illustration of a cross-sectional perspective view of the removable chromatic witness assembly 10, such as in the form of removable chromatic witness assembly 10g, of FIG. 4A coupled to the surface 16 of the composite structure 14, such as in the form of aircraft composite structure 14a. FIG. 4D is a schematic illustration of a cross-sectional perspective view of the removable chromatic witness assembly 10, such as in the form of removable chromatic witness assembly 10h, of FIG. 4B coupled to the surface 16 of the composite structure 14, such as in the form of aircraft composite structure 14a. The removable chromatic witness assembly 10 (see FIGS. 4C-4D) in the form of the removable chromatic witness applique 12 (see FIGS. 4C-4D) is configured to be removably applied directly and continuously to the surface 16 (see FIGS. 4C-4D) of the composite structure 14 (see FIGS. 4C-4D), and configured to monitor the thermal events 18 (see FIG. 8) and the impact events 20 (see FIG. 8) on the surface 16 (see FIGS. 4C-4D) of the composite structure 14 (see FIGS. 4C-4D). As shown in FIGS. 4C-4D, the second side 72b of the PSA layer 70 is coupled to the surface 16 of the composite structure 14.

Figure 5:
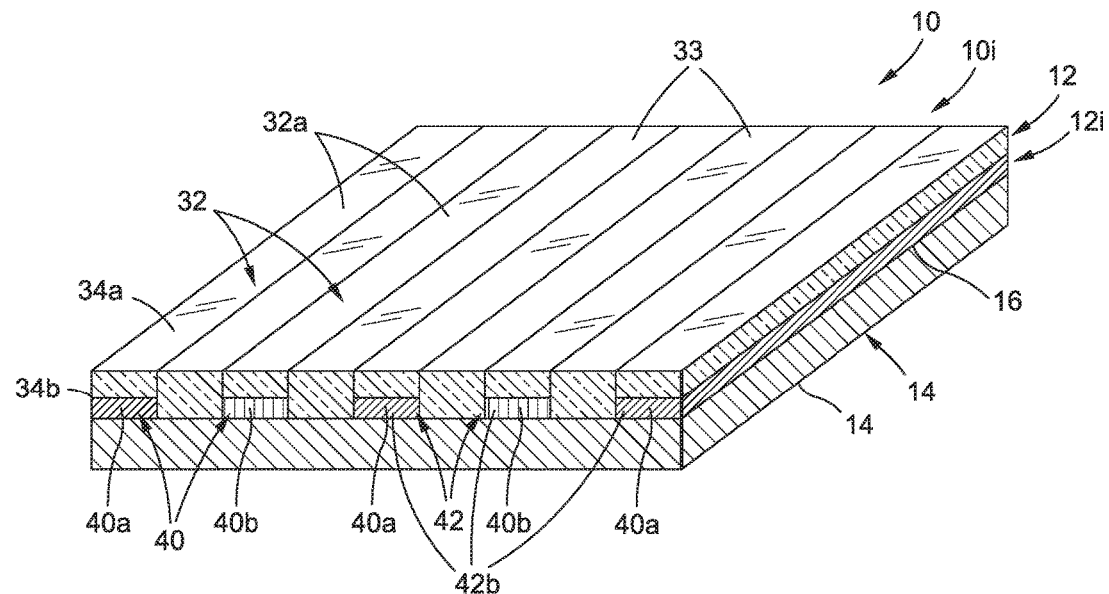
FIG. 5 is a schematic illustration of a cross-sectional perspective view of yet another embodiment of a removable chromatic witness assembly of the disclosure.

Now referring to FIG. 5, FIG. 5 is a schematic illustration of a cross-sectional perspective view of yet another embodiment of a removable chromatic witness assembly 10, such as in the form of removable chromatic witness assembly 10i, of the disclosure, coupled to the surface 16 of the composite structure 14, such as in the form of aircraft composite structure 14a. As shown in FIG. 5, the removable chromatic witness assembly 10, such as in the form of removable chromatic witness assembly 10i, comprises a removable chromatic witness applique 12, such as in the form of removable chromatic witness applique 12i.

FIG. 5 shows the removable chromatic witness assembly 10, such as in the form of removable chromatic witness assembly 10i, comprising a plurality of chromatic witness geometric configurations 40 separately coupled in arrangement 42, such as a nonadjacent repeating arrangement 42b, to the polymeric film layers 32, such as in the form of the high temperature polymeric film layer 32a, each having the first side 34a and the second side 34b. As shown in FIG. 5, the chromatic witness geometric configurations 40 comprise the first probe type 40a and the second probe type 40b in the nonadjacent arrangement 42b.

As further shown in FIG. 5, a plurality of filler elements 33 may be positioned between the plurality of chromatic witness geometric configurations 40 coupled to the polymeric film layers 32. The filler elements 33 (see FIG. 5) may comprise the same material as the polymeric film layer 32 (i.e., high temperature polymeric film, such as ethylene tetrafluoroethylene (ETFE) film, or another suitable polymeric film), or may comprise the same adhesive material 58 (see FIG. 8) (i.e., silicone, acrylic, epoxy adhesives, pressure sensitive adhesives (PSAs)), as one or more of the plurality of chromatic witness geometric configurations 40 but without any chromatic probes 50 (see FIG. 8). Alternatively, the filler elements 33 (see FIG. 5) may comprise another suitable material. Alternatively, no filler elements 33 may be present and air gaps (not shown) may be present between the chromatic witness geometric configurations 40 and attached polymeric film layers 32.

Figure 6:
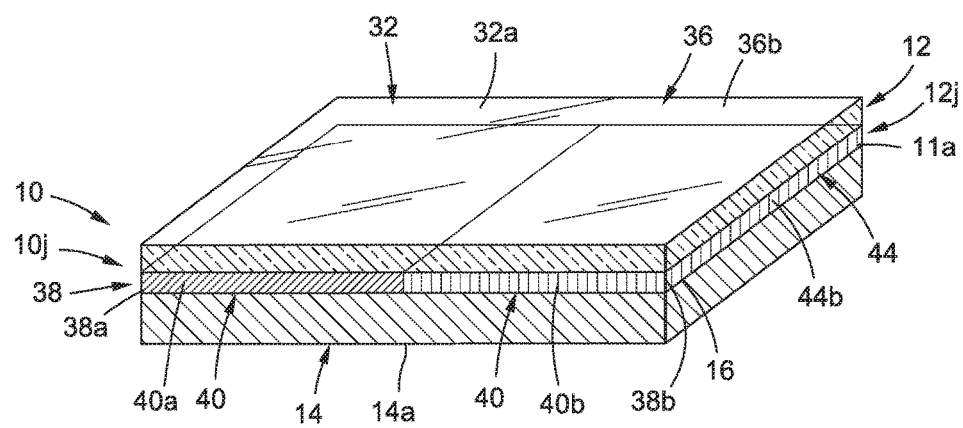
FIG. 6 is a schematic illustration of a cross-sectional perspective view of yet another embodiment of a removable chromatic witness assembly of the disclosure.

Now referring to FIG. 6, FIG. 6 is a schematic illustration of a cross-sectional perspective view of yet another embodiment of a removable chromatic witness assembly 10, such as in the form of removable chromatic witness assembly 10j, of the disclosure, coupled to the surface 16 of the composite structure 14, such as in the form of aircraft composite structure 14a. As shown in FIG. 6, the removable chromatic witness assembly 10, such as in the form of removable chromatic witness assembly 10j, comprises a removable chromatic witness applique 12, such as in the form of removable chromatic witness applique 12j.

As further shown in FIG. 6, the removable chromatic witness assembly 10, such as in the form of removable chromatic witness assembly 10j, comprises a 2-layer removable chromatic witness assembly 11a. The 2-layer removable chromatic witness assembly 11a (see FIG. 6) comprises the polymeric film layer 32, such as in the form of high temperature polymeric film layer 32a (see FIG. 6), coupled to the chromatic probe layer 38 (see FIG. 6). The polymeric film layer 32 (see FIG. 6) is comprised of portion 36, such as single portion 36b (see FIG. 1B), coupled to the chromatic witness geometric configurations 40 (see FIG. 6) of the chromatic probe layer 38 (see FIG. 6). The chromatic probe layer 38 (see FIG. 6) is a multi-probe layer 38a (see FIG. 6), such as in the form of a 2-probe layer 38b (see FIG. 6).

In this embodiment, as shown in FIG. 6, the chromatic witness geometric configurations 40 each have a geometric configuration 44 in the form of a square configuration 44b. The chromatic witness geometric configurations 40 (see FIG. 6) comprise the first probe type 40a (see FIG. 6) and the second probe type 40b (see FIG. 6) adjacent to each other. Each of the first probe type 40a and the second probe type 40b have different types 48b (see FIG. 8) of chromatic probes 50 (see FIG. 8). The removable chromatic witness assembly 10 (see FIG. 6), such as removable chromatic witness assembly 10j (see FIG. 6), comprising the removable chromatic witness applique 12 (see FIG. 6), such as removable chromatic witness applique 12j (see FIG. 6), is configured to be removably applied directly and continuously to the surface 16 (see FIG. 6) of the composite structure 14 (see FIG. 6), and configured to monitor the thermal events 18 (see FIG. 8) and the impact events 20 (see FIG. 8) on the surface 16 (see FIG. 6) of the composite structure 14 (see FIG. 6).

Referring now to FIG. 7, FIG. 7 is a schematic flowchart showing exemplary steps 80-92 of a method 79 of making an embodiment of a removable chromatic witness assembly 10 comprising a removable chromatic witness applique 12 of the disclosure. As shown in FIG. 7, the method 79 comprises a chromatic probe/adhesive mixing step 80, where a plurality of chromatic probes 50 are preferably dispensed from a probe dispenser 78 and mixed with an adhesive material 58, such as in the form of a pressure sensitive adhesive (PSA) 59. The chromatic probe/adhesive mixing step 80 (see FIG. 7) may use multiple series of chromatic probes 50 (see FIG. 7), for example, a first series of chromatic probes 50a (see FIG. 7), a second series of chromatic probes 50b (see FIG. 7), and a third series of chromatic probes 50c (see FIG. 7), each series of chromatic probes tailored to activate in a predefined time-temperature range 31 (see FIG. 8), when exposed to temperatures 26 (see FIG. 8) above predefined threshold temperatures 26a (see FIG. 8), or alternatively, tailored to monitor impact and activate when exposed to impacts 28 (see FIG. 8) above a predefined threshold impact 28a (see FIG. 8).

While three different series of chromatic probes 50 are used in the chromatic probe/adhesive mixing step 80 shown in FIG. 7, any number of chromatic probes 50, such as in the form of thermochromatic probes 54 (see FIG. 8) or mechanochromatic probes 56 (see FIG. 8) may be used to take thermal testing measurements 18a (see FIG. 8) or impact testing measurements 20a (see FIG. 8), respectively, on the surface 16 (see FIGS. 3C, 4C, 7) of the structure 14 (see FIGS. 3C, 4C, 7) over which the removable chromatic witness applique 12 (see FIGS. 3C, 4C, 7) is applied.

As shown in the chromatic probe/adhesive mixing step 80 (see FIG. 7), the adhesive material 58 (see FIG. 7) may comprise different adhesives 58 (see FIG. 7), such as silicone adhesive 58a (see FIG. 7), acrylic adhesive 58b (see FIG. 7), and epoxy adhesive 58c (see FIG. 7). Alternatively, some or all of each adhesive material 58 (see FIG. 7) used may be the same type of adhesive material 58 (see FIG. 7), or a mixture of two more adhesive materials 58 (see FIG. 7).

As shown in the chromatic probe/adhesive mixing step 80 (see FIG. 7), the first series of chromatic probes 50a (see FIG. 7) is mixed with the silicone adhesive 58a (see FIG. 7) to form, as shown in a removable chromatic witness assembly forming step 82 (see FIG. 7) of the method 79, a chromatic witness geometric configuration 40 (see FIG. 7) of a first probe type 40a (see FIG. 7). As further shown in step 80 (see FIG. 7), the second series of chromatic probes 50b (see FIG. 7) is mixed with the acrylic adhesive 58b (see FIG. 7) to form, as shown in the removable chromatic witness assembly forming step 82 (see FIG. 7), a chromatic witness geometric configuration 40 (see FIG. 7) of a second probe type 40b (see FIG. 7). As further shown in step 80 (see FIG. 7), the third series of chromatic probes 50c (see FIG. 7) is mixed with the epoxy adhesive 58c (see FIG. 7) to form, as shown in the removable chromatic witness assembly forming step 82 (see FIG. 7), a chromatic witness geometric configuration 40 (see FIG. 7) of a third probe type 40c (see FIG. 7). The chromatic witness geometric configurations 40 (see FIG. 7) contain different ranges or types of chromatic material 51 (see FIG. 8) mixed into the adhesive material 58 (see FIG. 7).

As shown in FIG. 7, the method 79 further comprises the removable chromatic witness assembly forming step 82 (see FIG. 7), where a polymeric film layer 32 is applied over each of the three chromatic witness geometric configurations 40 to form three removable chromatic witness assemblies 10. As discussed in detail above, the polymeric film layer 32 (see FIG. 7) preferably comprises a high temperature polymeric film layer 32a (see FIGS. 3A, 4A), such as ethylene tetrafluoroethylene (ETFE) film or another suitable polymeric film, that is stable in a temperature range of between about 130° F. (one hundred thirty degrees Fahrenheit) to about 500° F. (five hundred degrees Fahrenheit). Preferably, the polymeric film layer 32 (see FIG. 7) is optically transparent.

As shown in FIG. 7, the method 79 further comprises an exemplary rectangular strip formation step 84, where the removable chromatic witness assemblies 10 may be slit, cut, or otherwise divided or formed into rectangular strips 44a of the first probe type 40a with the attached polymeric film layers 32, of the second probe type 40b with the attached polymeric film layers 32, and of the third probe type 40c with the attached polymeric film layers 32. In the rectangular strip formation step 84 (see FIG. 7), the removable chromatic witness assemblies 10 (see FIG. 7) may be slit, cut, or otherwise divided or formed into rectangular strips 44a (see FIG. 7) having a width of about 0.5 inch or greater, or another suitable width.

As shown in FIG. 7, the method 79 further comprises an exemplary backing film application step 86, where one of each of the rectangular strips 44a of the first probe type 40a, the second probe type 40b, and the third probe type 40c are applied to and over a backing film layer 60. The rectangular strips 44a (see FIG. 7) are positioned in an arrangement 42 (see FIG. 2A), such as an adjacent repeating arrangement 42a (see FIG. 2A) (or alternatively, a nonadjacent repeating arrangement 42b (see FIG. 5)), on the backing film layer 60 (see FIG. 7). As discussed above in detail, the backing film layer 60 (see FIG. 7) may comprise a high temperature polymeric film layer, such as ethylene tetrafluoroethylene (ETFE) film, or another suitable polymeric film, that is stable in a temperature range of between about 130° F. to about 500° F. Preferably, the backing film layer 60 (see FIG. 7) is optically transparent and may be dual etched. The backing film layer 60 (see FIG. 7) may have a width of 3 inches, a width of 4 inches, a width of 12 inches wide, or another suitable width.

As shown in FIG. 7, the method 79 further comprises an exemplary pressure sensitive adhesive (PSA) application step 88, where a pressure sensitive adhesive (PSA) layer 70 is applied to the backing film layer 60 having the attached chromatic witness geometric configurations 40 and the polymeric film layers 32 to form the removable chromatic witness assembly 10 comprising the removable chromatic witness applique 12, configured for application over the surface 16 of the composite structure 14. The removable chromatic witness assembly 10 (see FIG. 7) comprising the removable chromatic witness applique 12 (see FIG. 7) having four layers may be formed in rolls, such as in a tape form, or another suitable form.

As shown in FIG. 7, the method 79 may further optionally comprise an exemplary testing step 90, where the removable chromatic witness assembly 10 comprising the removable chromatic witness applique 12 is applied over the composite structure 14 and subjected to a test 156 (see FIG. 8), such as a flight test 156a (see FIG. 8), and is exposed to a heat source 94 that may have high temperatures. As shown in the exemplary testing step 90 (see FIG. 7), in this embodiment, the removable chromatic witness assembly 10 (see FIG. 7) comprising the removable chromatic witness applique 12 (see FIG. 7) comprises the pressure sensitive adhesive (PSA) layer 70 (see FIG. 7) adjacent the composite structure 14 (see FIG. 7), the backing film layer 60 (see FIG. 7) adjacent the PSA layer 70 (see FIG. 7), the chromatic witness geometric configurations 40 (see FIG. 7) comprising the first probe type 40a (see FIG. 7), the second probe type 40b (see FIG. 7), and the third probe type 40c (see FIG. 7), adjacent the backing film layer 60 (see FIG. 7), and the polymeric film layers 32 (see FIG. 7) adjacent the chromatic witness geometric configurations 40 (see FIG. 7).

As shown in FIG. 7, the method 79 may further optionally comprise an exemplary illumination step 92. In the optional illumination step 92 (see FIG. 7), the removable chromatic witness assembly 10 (see FIG. 7) comprising the removable chromatic witness applique 12 (see FIG. 7) that has undergone the testing step 90 (see FIG. 7) is illuminated with a light source 96 (see FIG. 7) that emits illumination 98 (see FIG. 7) over the surface 16 (see FIG. 7) of the composite structure 14 (see FIG. 7), such as in the form of an aircraft composite structure 14a (see FIG. 7), covered with the removable chromatic witness assembly 10 (see FIG. 7) comprising the removable chromatic witness applique 12 (see FIG. 7).

Now referring to FIG. 8, FIG. 8 is an illustration of a functional block diagram showing exemplary embodiments of a removable chromatic witness system 100 of the disclosure. As shown in FIG. 8, the removable chromatic witness system 100 comprises a composite structure 14 having a surface 16 to be tested and monitored for one of, thermal events 18 and impact events 20. The composite structure 14 (see FIG. 8) may comprise an aircraft composite structure 14a (see FIG. 8), such as a carbon fiber reinforced polymer (CFRP) part 14b (see FIG. 8).

As shown in FIG. 8, the removable chromatic witness system 100 further comprises a removable chromatic witness assembly 10, such as in the form of a removable chromatic witness applique 12, as discussed in detail above, applied directly and continuously over the surface 16 of the composite structure 14 to be tested and monitored for the thermal events 18 and/or the impact events 20.

Preferably, and the removable chromatic witness applique 12 (see FIG. 8) is a multi-sensing applique 13 (see FIG. 8) configured to take thermal testing measurements 18a (see FIG. 8) and impact testing measurements 20a (see FIG. 8) across the surface 16 (see FIG. 8) of the composite structure 14 (see FIG. 8) over which the removable chromatic witness applique 12 (see FIG. 8) is applied.

As shown in FIG. 8, and discussed above, the removable chromatic witness assembly 10 comprises the chromatic probe layer 38 comprised of the plurality of chromatic witness geometric configurations 40 separately coupled in the repeating arrangement 42 (see FIGS. 1A, 2A) to one or more portions 36 (see FIGS. 1A, 2A) of a polymeric film layer 32, such as a high temperature polymeric film layer 32a. The chromatic probe layer 38 may comprise a multi-probe layer 38a, such as a 2-probe layer 38b, a 3-probe layer 38c, or another suitable number of chromatic probes 50.

As shown in FIG. 8, the plurality of chromatic witness geometric configurations 40 have a geometric configuration 44, such as in the form of a rectangular strip 44a, a square configuration 44b, or another suitable configuration or shape. Each chromatic witness geometric configuration 40 comprises a plurality of chromatic probes 50 comprised of a chromatic material 51, and of a same type 48a incorporated into the adhesive material 58. At least two of the plurality of chromatic witness geometric configurations 40 have a different type 48b of chromatic probes 50 with a different sensing capability 52 for sensing one of, the thermal events 18 and the impact events 20 on the surface 16 of the composite structure 14.

As shown in FIG. 8, the chromatic probes 50 may comprise thermochromatic probes 54 made of a thermochromatic material 54a, and mechanochromatic probes 56 made of a mechanochromatic material 56a. The chromatic probes 50 are preferably tailored to activate at predefined time-temperature ranges 31. When the thermochromatic material 54 is activated by exposure to the temperatures 26 to which it has been tailored, the thermochromatic probes 54 undergoes fluorescent shifts. When illuminated by a light source 96 of a suitable wavelength, the fluorescent shifts in the chromatic material 51 become visible, manifesting themselves as chromatic response 22, such as color changes 24 or intensity changes 25. For example, the UV light source 96a may have a wavelength in a range of 10 nm (nanometers) to 600 nm, and preferably, a wavelength in a range of 100 nm to 400 nm, for fluorescent activation of the chromatic material 51.

As shown in FIG. 8, the chromatic probes 50 are mixed with an adhesive material 58 preferably in the form of a pressure sensitive adhesive (PSA) 59. The adhesive material 58 may comprise a silicone adhesive 58a, an acrylic adhesive 58b, an epoxy adhesive 58c, or another suitable adhesive material 58.

In one embodiment, the removable chromatic witness assembly 10 (see FIG. 8) is a 2-layer removable chromatic witness assembly 11a (see FIG. 1A) comprising the plurality of chromatic witness geometric configurations 40 in the chromatic probe layer 38 coupled to the polymeric film layer or layers 32 (see FIG. 8). In another embodiment, the removable chromatic witness assembly 10 (see FIG. 8) is a 4-layer removable chromatic witness assembly 11b (see FIG. 1A) comprising the plurality of chromatic witness geometric configurations 40 (see FIG. 8) in the chromatic probe layer 38 (see FIG. 8) coupled to the polymeric film layer or layers 32 (see FIG. 8) and coupled to a backing film layer 60 (see FIG. 8) and a pressure sensitive adhesive (PSA) layer 70 (see FIG. 8). The backing film layer 60 is coupled to the plurality of chromatic witness geometric configurations 40, and the pressure sensitive adhesive (PSA) layer 70 is coupled to the backing film layer 60.

As shown in FIG. 8, the removable chromatic witness system 100 further comprises a light source 96 configured to activate the plurality of chromatic probes 50 in the removable chromatic witness applique 12 applied to the composite structure 16. Each different type 48a of chromatic probe 50 is configured to fluoresce in a different predefined time-temperature range 31, in response to the light source 96. The light source 96 may comprise one of, an ultraviolet (UV)

light source 96a, a light-emitting diode (LED) light source 96b, an infrared (IR) light source 96c, or another suitable light source 96.

The light source 96 (see FIGS. 8-10) illuminates the removable chromatic witness assembly 10 (see FIG. 8) comprising the removable chromatic witness applique 12 (see FIG. 8) with illumination 98 (see FIGS. 9-10) of light of a preselected wavelength, such as in the ultraviolet (UV) or infrared (IR) range. The light source 96 (see FIG. 8) is configured to activate the chromatic material 51 of the removable chromatic witness assembly 10 comprising the removable chromatic witness applique 12 to prompt an onset of color changes 24 (see FIG. 8) and intensity changes 25 (see FIG. 8) in the chromatic material 51. The color changes 24 and intensity changes 25 in the chromatic probes 50 are preferably used to map a temperature profile 26c (see FIG. 8) over time 30 (see FIG. 8) of the composite structure 14, and may indicate that the composite structure 14 has been subjected to temperatures 26 (see FIG. 8) that exceed predefined threshold temperatures 26a (see FIG. 8) outside a desired temperature range 26b (see FIG. 8) and exceed a predefined time period 30a (see FIG. 8), or exceed a predefined threshold impact 28a (see FIG. 8). The chromatic probes 50 (see FIG. 8) act as a "witness" to monitor temperatures 26a (see FIG. 8) of the composite structure 14 (see FIG. 8) during tests 156 (see FIG. 8), such as a flight test 156a (see FIG. 8), a thermal test 156b (see FIG. 8), an impact test 156c (see FIG. 8), or another suitable test.

As shown in FIG. 8, the removable chromatic witness system 100 further comprises an imaging device 106 configured to image and record one or more images 104 (see FIG. 9) of a chromatic response 22 of the different types 48b of chromatic probes 50 to the light source 96. The chromatic response 22 comprises one or more color changes 24 and one or more intensity changes 25. The imaging device 106 may comprise one of, a detector 106a (see FIG. 8), including a spectrometer 106b (see FIG. 8), a camera 106c (see FIG. 8), including a digital camera 106d (see FIG. 8), or another suitable imaging device 106.

As shown in FIG. 8, the removable chromatic witness system 100 further comprises a data processor system 110, such as in the form of a computer 112. The data processor system 110 (see FIG. 8), such as in the form of computer 112 (see FIG. 8), is configured for processing and analyzing the one or more images 104 (see FIG. 9) of the removable chromatic witness assembly 10 (see FIG. 8) to identify any areas 102 (see FIG. 9) on the surface 16 (see FIGS. 8, 9) of the composite structure 14 (see FIGS. 8, 9) that have experienced one of, temperatures 26 (see FIG. 8) above a predefined threshold temperature 26a (see FIG. 8), and impacts 28 (see FIG. 8) above a predefined threshold impact 28a (see FIG. 8). The removable chromatic witness applique 12 is being imaged to indicate the heat or thermal exposure and/or impact exposure of the surface 16 of the composite structure 14. The computer 112 (see FIG. 8) may be used to store the one or more images 104 (see FIG. 9) in a memory. Based on the one or more images 104 (see FIG. 9) recorded by the imaging device 106 (see FIG. 8), such as the camera 106c (see FIG. 8), the computer 112 (see FIG. 8) may process and analyze the one or more images 104 (see FIG. 9) and other data generated during testing of the composite structure 14 (see FIG. 8).

After the composite structure 14 (see FIG. 8) is tested, the removable chromatic witness applique 12 (see FIG. 8) may be removed for illumination with a light source 96 (see FIG. 8) and processing and analysis. Alternatively, after the composite structure 14 (see FIG. 8) is tested, the removable chromatic witness applique 12 (see FIG. 8) may be illuminated with the light source 96 (see FIG. 8) while still attached to the composite structure 14 (see FIG. 8), and then removed at a later time for processing and analysis.

As shown in FIG. 8, the removable chromatic witness system 100 may further comprise a calibration 152 of the removable chromatic witness assembly 10 applied to the composite structure 14 that may preferably use one or more thermocouples 154.

Referring now to FIG. 9, FIG. 9 is a schematic representation of an exemplary embodiment of a removable chromatic witness system 100, such as in the form of removable chromatic witness system 100a, of the disclosure, showing areas 102 illuminated by the light source 96, such as in the form of ultraviolet (UV) light source 96a. As shown in FIG. 9, the removable chromatic witness assembly 10 comprising the removable chromatic witness applique 12 comprises the four layers of the polymeric film layer 32 over the chromatic witness geometric configurations 40 of the chromatic probe layer 38 (see FIG. 8), the backing film layer 60, and the pressure sensitive adhesive layer (PSA) 70, all over the surface 16 of the composite structure 14.

After the removable chromatic witness assembly 10 (see FIG. 9) comprising the removable chromatic witness applique 12 (see FIG. 9) applied over the surface 16 (see FIG. 9) of the composite structure 14 (see FIG. 9) has undergone a test 156 (see FIG. 8), such as a flight test 156a (see FIG. 8), a thermal test 156b (see FIG. 8), an impact test 156c (see FIG. 8), or another suitable test, or has undergone monitoring, the surface 16 (see FIG. 9) of the composite structure 14 (see FIG. 9) covered with the removable chromatic witness assembly 10 (see FIG. 9) comprising the removable chromatic witness applique 12 (see FIG. 9) is illuminated with the light source 96 (see FIG. 9). Alternatively, the removable chromatic witness assembly 10 (see FIG. 9) comprising the removable chromatic witness applique 12 (see FIG. 9) may be removed from the composite structure 14 (see FIG. 9) and illuminated off the composite structure 14 (see FIG. 9) at a later time or in another location.

As shown in FIG. 9, in this embodiment, the light source 96 activates any areas 102 where the chromatic probes 50 (see FIG. 8) in the first probe type 40a such as area 102a, the second probe type 40b such as area 102b, and the third probe type 40c such as area 102c, of the chromatic witness geometric configurations 40, have been exposed to temperatures 26 (see FIG. 8) exceeding predefined threshold temperatures 26a (see FIG. 8) in predefined time-temperature ranges 31 (see FIG. 8). The light source 96 (see FIG. 9), such as in the form of ultraviolet (UV) light source 96a (see FIG. 9) illuminates the areas 102 (see FIG. 9) with illumination 98 (see FIG. 9) of light of a preselected wavelength, such as in the ultraviolet (UV) range.

As shown in FIG. 9, the imaging device 106 images and records one or more images 104 of the areas 102, after activation with the light source 96. Results of any color changes 24 (see FIG. 8) and intensity changes 25 (see FIG. 8) may be imaged or photographed with the imaging device 106 (see FIG. 8), recorded, and documented.

As further shown in FIG. 9, the imaging device 106 is connected to a data processor system 110 via a connection element 108, such as a wired or wireless connection. The data processor system 110 preferably comprises a computer 112 that may be used to store the one or more images 104 in a memory. Based on the one or more images 104 (see FIG. 9) imaged and recorded by the imaging device 106 (see FIG. 9), the data processor system 110, such as in the form of computer 112 (see FIG. 9) may process and analyze the one or more images 104 to provide information regarding areas 102 adversely exposed to thermal events 18 (see FIG. 8) and impact events 20 (see FIG. 8), and to provide information regarding thermal testing measurements 18*a* (see FIG. 8) and impact testing measurements 20*a* (see FIG. 8) measured by the removable chromatic witness assembly 10 (see FIG. 8) comprising the removable chromatic witness applique 12 (see FIG. 8).

Now referring to FIG. 10, FIG. 10 is a schematic representation of another exemplary embodiment of a removable chromatic witness system 100, such as in the form of removable chromatic witness system 100*b*, of the disclosure, that uses a portable probe device 116 to illuminate a sample 128, such as a sample of the removable chromatic witness assembly 10 (see FIG. 8) comprising the removable chromatic witness applique 12 (see FIG. 8) removed from the composite structure 14 (see FIG. 8). The portable probe device 116 (see FIG. 10) may be adapted for field use or another suitable use.

As shown in FIG. 10, the removable chromatic witness system 100, such as in the form of removable chromatic witness system 100*b*, comprises the light source 96, such as in the form of light-emitting diode (LED) light source 96*b*, that provides illumination 98 as an input 114*a* into the portable probe device 116. As further shown in FIG. 10, the portable probe device 116, in one embodiment, comprises a plurality of illumination fibers 118 such as optical illumination fibers, and a pickup fiber 118, such as an optical pickup fiber, preferably centered among the illumination fibers 118. The illumination fibers 118 emit light beams 122 (see FIG. 10) that provide an excitation light 124 (see FIG. 10) on the sample 128 to activate the chromatic probes 50 in the sample 128 to give off a fluorescence emission 126 (see FIG. 10). The fluorescence emission 126 is picked up by the pickup fiber 118 and transmitted as an output 114*b* (see FIG. 10) from the portable probe device 116 as one or more images 104 imaged and recorded by the imaging device 106, such as in the form of a detector 106*a* (see FIG. 10).

As further shown in FIG. 10, the imaging device 106, such as in the form of a detector 106*a*, is connected to the data processor system 110, such as in the form of computer 112, via the connection element 108, such as a wired or wireless connection. Based on the one or more images 104 imaged and recorded by the imaging device 106, the data processor system 110, such as in the form of computer 112, may process and analyze the one or more images 104 of the fluorescence emission 126 to provide information regarding thermal testing measurements 18*a* (see FIG. 8) and impact testing measurements 20*a* (see FIG. 8) measured by the removable chromatic witness assembly 10 (see FIG. 8) comprising the removable chromatic witness applique 12 (see FIG. 8).

Figure 11:
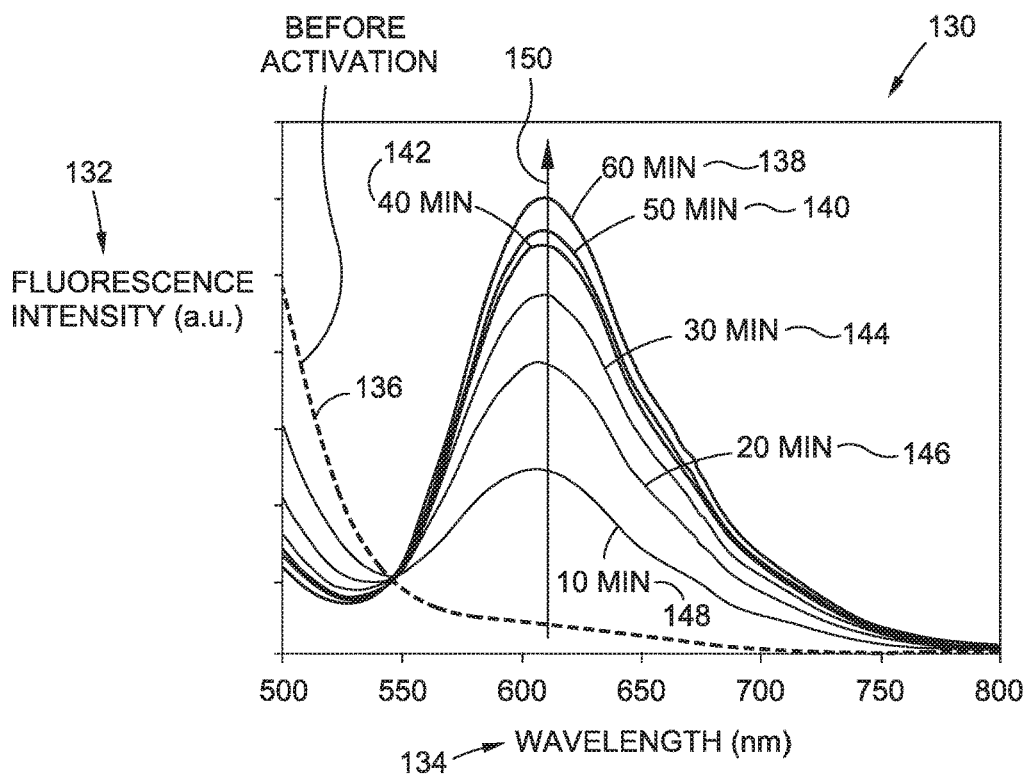
FIG. 11 is a graph showing representative plots of fluorescence intensity versus wavelength of activated chromatic probes.

Referring now to FIG. 11, FIG. 11 is a graph 130 showing representative plots of fluorescence intensity 132 in arbitrary units (a.u.) versus wavelength 134 in nanometers (nm) of activated chromatic probes 50 exposed for various times 30 (see FIG. 8) above a predefined threshold temperature 26*a* (see FIG. 8). As shown in FIG. 11, the plots include a plot 136 of chromatic probes 50 (see FIG. 8) before activation, a plot 138 of chromatic probes 50 (see FIG. 8) exposed above the predefined threshold temperature 26*a* (see FIG. 8) for 60 minutes, a plot 140 of chromatic probes 50 (see FIG. 8) exposed above the predefined threshold temperature 26*a* (see FIG. 8) for 50 minutes, a plot 142 of chromatic probes 50 (see FIG. 8) exposed above the predefined threshold temperature 26*a* (see FIG. 8) for 40 minutes, a plot 144 of chromatic probes 50 (see FIG. 8) exposed above the predefined threshold temperature 26*a* (see FIG. 8) for 30 minutes, a plot 146 of chromatic probes 50 (see FIG. 8) exposed above the predefined threshold temperature 26*a* (see FIG. 8) for 20 minutes, and a plot 148 of chromatic probes 50 (see FIG. 8) exposed above the predefined threshold temperature 26*a* (see FIG. 8) for 10 minutes. In this example, as shown in FIG. 11, the peak intensities 150 of fluorescence intensity 132 at about a 610 wavelength may be used to determine a percentage of chromatic probes 50 (see FIG. 8) that have been activated.

Figure 12:
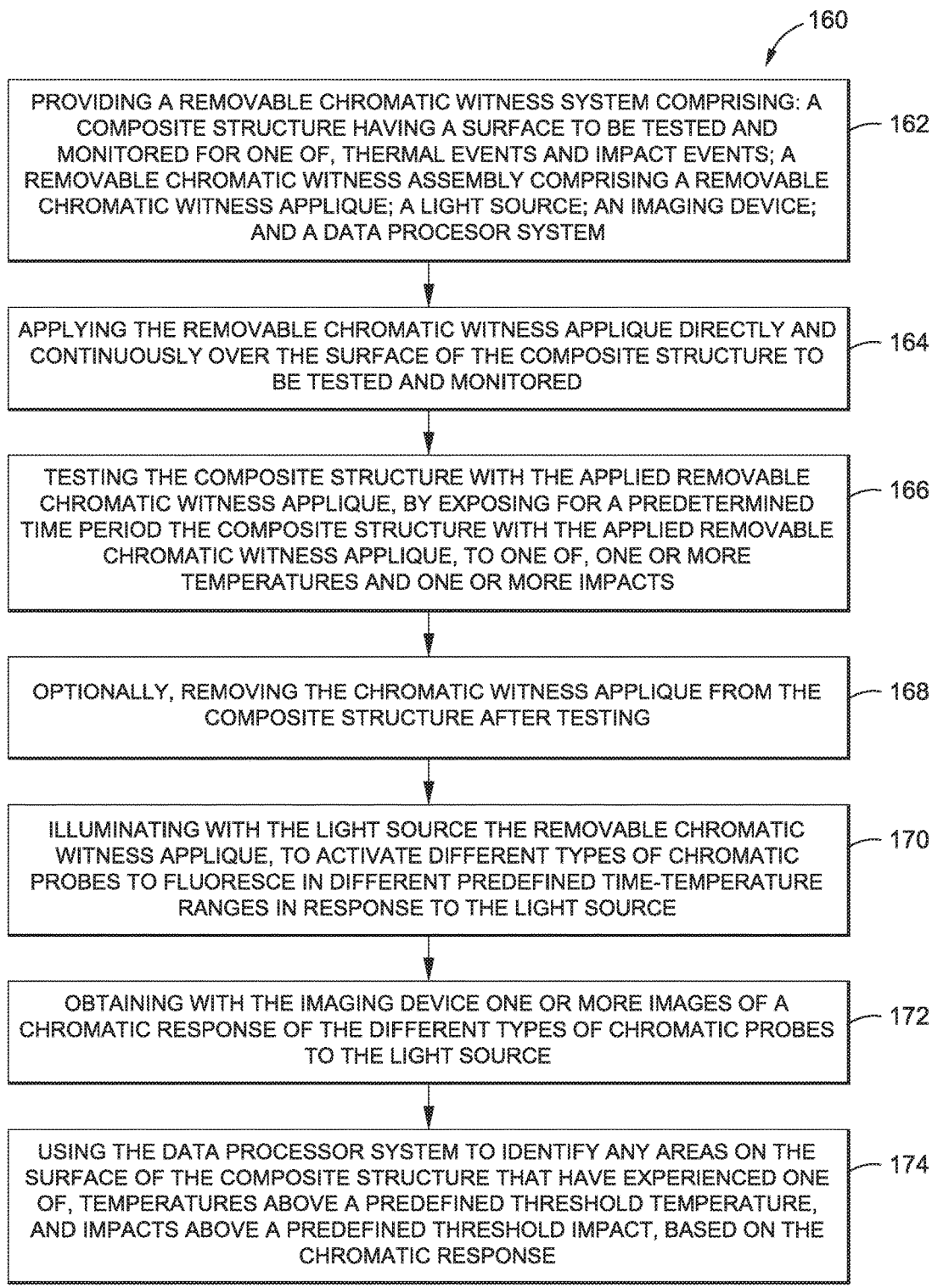
FIG. 12 is an illustration of an exemplary flowchart showing a method of using a removable chromatic witness system of the disclosure to monitor thermal events and impact events on a composite structure.

Referring now to FIG. 12, in another embodiment, as shown in FIG. 12, there is provided a method 160 of using an embodiment of the removable chromatic witness system 100 (see FIGS. 8-10) to monitor thermal events 18 (see FIG. 8) and impact events 20 (see FIG. 8) on a surface 16 (see FIGS. 8, 9) of the composite structure 14 (see FIG. 8). FIG. 12 is an illustration of an exemplary flowchart showing the method 160 of using the removable chromatic witness system 100 (see FIG. 8) to monitor the thermal events 18 (see FIG. 8) and the impact events 20 (see FIG. 8) on the surface 16 (see FIGS. 8, 9) of the composite structure 14 (see FIGS. 8, 9), in accordance with the disclosure.

As shown in FIG. 12, the method 160 comprises step 162 of providing the removable chromatic witness system 100 (see FIGS. 8-10). As discussed above, the removable chromatic witness system 100 (see FIGS. 8-10) comprises the composite structure 14 (see FIGS. 8, 9) having the surface 16 (see FIGS. 8, 9) to be tested and monitored for one of, thermal events 18 (see FIG. 8) and impact events 20 (see FIG. 8). The composite structure 14 (see FIGS. 8, 13) may comprise an aircraft composite structure 14*a* (see FIGS. 8, 13).

The removable chromatic witness system 100 (see FIG. 8) further comprises the removable chromatic witness assembly 10 (see FIG. 8) comprising the removable chromatic witness applique 12 (see FIG. 8) having the plurality of chromatic witness geometric configurations 40 (see FIG. 8) separately coupled in a repeating arrangement 42 (see FIG. 8) to one or more portions 36 (see FIGS. 1A-4B) of the polymeric film layer 32 (see FIGS. 1A-4B, 8). Each chromatic witness geometric configuration 40 (see FIG. 8) comprises the plurality of chromatic probes 50 (see FIG. 8) of a same type 48*a* (see FIG. 8) incorporated into the adhesive material 58 (see FIG. 8). At least two of the plurality of chromatic witness geometric configurations 40 (see FIG. 8) have a different type 48*b* (see FIG. 8) of chromatic probes 50 (see FIG. 8) with a different sensing capability 52 (see FIG. 8) for sensing one of, the thermal events 18 (see FIG. 8) and the impact events 20 (see FIG. 8) on the surface 16 (see FIG. 8) of the composite structure 14 (see FIG. 8). As discussed above in detail, the removable chromatic witness system 100 (see FIG. 8) further comprises a light source 96 (see FIG. 8), an imaging device 106 (see FIG. 8), and a data processor system 110 (see FIG. 8).

The step 162 (see FIG. 12) of providing the removable chromatic witness system 100 (see FIG. 8) may comprise providing the removable chromatic witness applique 12 (see FIG. 8) with the backing film layer 60 (see FIG. 8) and the pressure sensitive adhesive (PSA) layer 70 (see FIG. 8). The backing film layer 60 (see FIG. 8) is coupled to the plurality of chromatic witness geometric configurations 40 (see FIG. 8), and the pressure sensitive adhesive (PSA) layer 70 (see FIG. 8) is coupled to the backing film layer 60 (see FIG. 8).

The step 162 (see FIG. 12) of providing the removable chromatic witness system 100 (see FIG. 8) may further comprise providing the removable chromatic witness applique 12 (see FIG. 8) with three repeating chromatic witness geometric configurations 40d (see FIG. 2A). Each of the three repeating chromatic witness geometric configurations 40d (see FIG. 2A) have different types 48b (see FIG. 8) of chromatic probes 50 (see FIG. 8) configured to fluoresce at three different time-temperature ranges 31 (see FIG. 8).

As shown in FIG. 12, the method 160 further comprises step 164 of applying the removable chromatic witness applique 12 (see FIG. 8) directly and continuously over the surface 16 (see FIG. 8) of the composite structure 14 (see FIG. 8) to be tested and monitored.

As shown in FIG. 12, the method 160 further comprises step 166 of testing the composite structure 14 (see FIG. 8) with the applied removable chromatic witness applique 12 (see FIG. 8), by exposing for a predefined time period 30a (see FIG. 8) the composite structure 14 (see FIG. 8) with the applied removable chromatic witness applique 12 (see FIG. 8), to one of, one or more temperatures 26 (see FIG. 8), and one or more impacts 28 (see FIG. 8).

The step 166 (see FIG. 12) of testing the composite structure 14 (see FIG. 8) with the applied removable chromatic witness applique 12 (see FIG. 8) comprises testing an aircraft composite structure 14a (see FIGS. 8, 13) by conducting a test 156 (see FIG. 8) comprising one of, a flight test 156a (see FIG. 8), a thermal test 156b (see FIG. 8), an impact test 156c (see FIG. 8), or another suitable test.

As shown in FIG. 12, the method 160 further comprises, optionally, step 168 of removing the chromatic witness applique 12 (see FIG. 8) from the composite structure 14 (see FIG. 8) after testing 166 of the composite structure 14 (see FIG. 8). Alternatively, the chromatic witness applique 12 (see FIG. 8) may remain applied to the composite structure 14 and removed at a later time.

As shown in FIG. 12, the method 160 further comprises step 170 of illuminating with the light source 96 (see FIGS. 8-10) the removable chromatic witness applique 12 (see FIG. 8), to activate the different types 48b (see FIG. 8) of chromatic probes 50 (see FIG. 8) to fluoresce in different predefined time-temperature ranges 31 (see FIG. 8), in response to the light source 96 (see FIG. 8).

As shown in FIG. 12, the method 160 further comprises step 172 of obtaining with the imaging device 106 (see FIGS. 8-10) one or more images 104 (see FIGS. 9-10) of a chromatic response 22 (see FIG. 8) of the different types 48b (see FIG. 8) of chromatic probes 50 (see FIG. 8) to the light source 96 (see FIG. 8). The chromatic response 22 (see FIG. 8) comprises one or more color changes 24 (see FIG. 8) and one or more intensity changes 25 (see FIG. 8).

As shown in FIG. 12, the method 160 further comprises step 174 of using the data processor system 110 (see FIGS. 8-10) to identify areas 102 (see FIG. 9) on the surface 16 (see FIG. 9) of the composite structure 14 (see FIG. 9) that have experienced one of, temperatures 26 (see FIG. 8) above a predefined threshold temperature 26a (see FIG. 8), and impacts 28 (see FIG. 8) above a predefined threshold impact 28a (see FIG. 8), based on the chromatic response 22 (see FIG. 8).

The method 160 (see FIG. 12) may further comprise, prior to testing 166 (see FIG. 12) the composite structure 14 (see FIG. 8) with the applied removable chromatic witness applique 12 (see FIG. 8), conducting a calibration 152 (see FIG. 8) of the plurality of chromatic probes 50 (see FIG. 8) in the removable chromatic witness applique 12 (see FIG. 8) applied over the surface 16 (see FIG. 8) of the composite structure 14 (see FIG. 8), using one or more thermocouples 154 (see FIG. 8) attached to the composite structure 14 (see FIG. 8).

Figure 13:
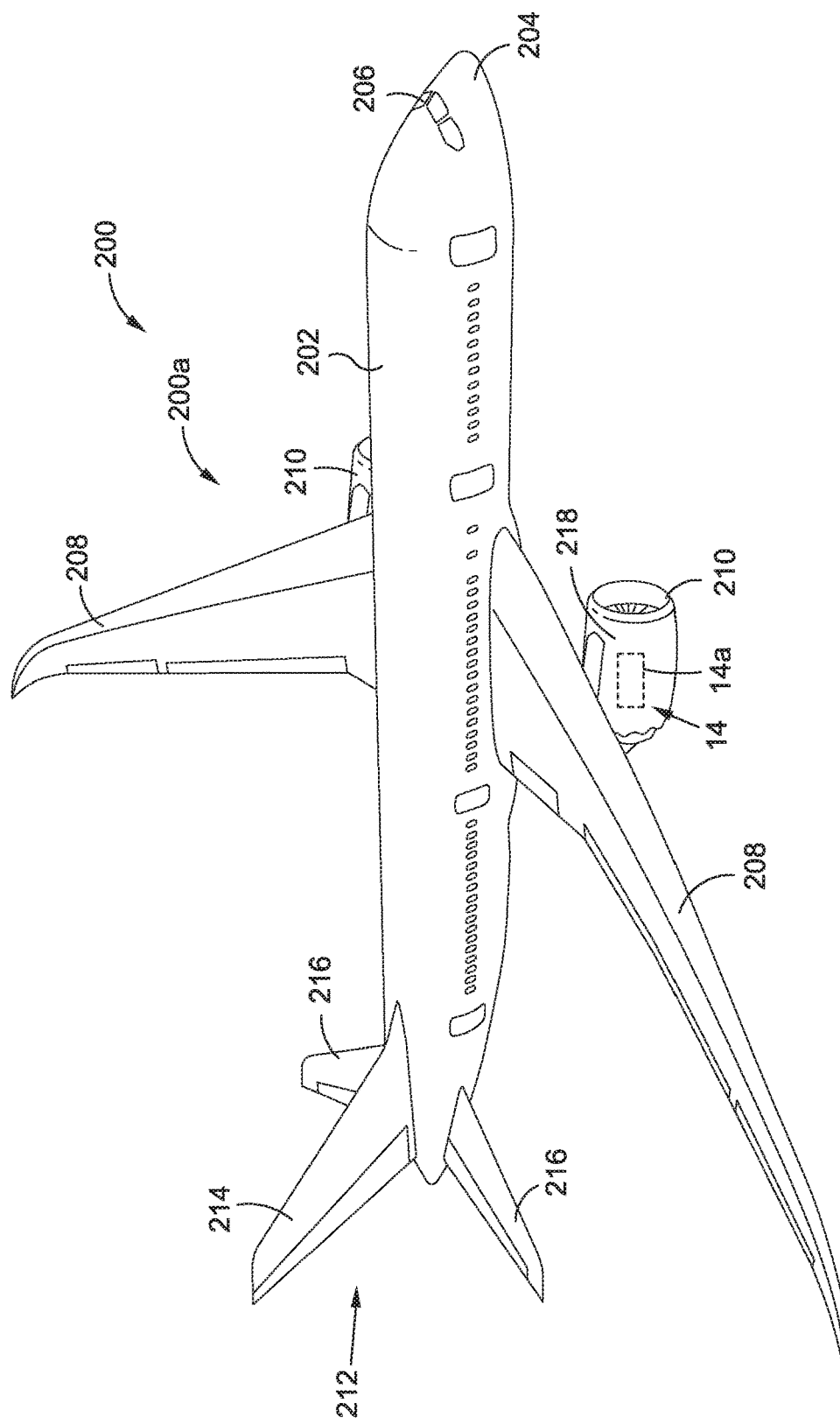
FIG. 13 is an illustration of a perspective view of an air vehicle that incorporates one or more composite structures that may be tested or monitored with embodiments of the removable chromatic witness assembly, removable chromatic witness system, and method of the disclosure.

Now referring to the FIG. 13, FIG. 13 is an illustration of a perspective view of an air vehicle 200, such as in the form of aircraft 200a, that incorporates one or more composite structures 14, such as aircraft composite structures 14a, that may be tested or monitored with embodiments of the removable chromatic witness assembly 10 (see FIGS. 1A-7), removable chromatic witness system 100 (see FIGS. 8-10), and method 160 (see FIG. 12) of the disclosure. As shown in FIG. 13, the air vehicle 200, such as in the form of aircraft 200a, comprises a fuselage 202, a nose 204, a cockpit 2016, wings 208, engines 210, and an empennage 212 comprising horizontal stabilizers 214 and a vertical stabilizer 216.

As further shown in FIG. 13, the air vehicle 200, such as in the form of aircraft 200a, comprises one or more composite structures 14, such as in the form of an aircraft composite structure 14a, for example, carbon fiber reinforced polymer (CFRP) parts 14b (see FIG. 8), that may be tested and monitored using embodiments of the removable chromatic witness assembly 10 (see FIGS. 1A-7), the removable chromatic witness system 100 (see FIGS. 8-10), and the method 160 (see FIG. 12), of the disclosure. In an exemplary embodiment, the composite structure 14 (see FIGS. 8, 13) comprises the aircraft composite structure 14a (see FIGS. 8, 13), such as a thrust reverser 218 (see FIG. 13) on the air vehicle 200 (see FIG. 13). For example, the removable chromatic witness assembly 10 (see FIGS. 1A-6), the removable chromatic witness system 100 (see FIGS. 8-10), and the method 160 (see FIG. 12), of the disclosure may be used to test, monitor, and improve an insulation blanket structure for a thrust reverser inner wall of the thrust reverser 218 (see FIG. 13). In other embodiments (not shown), the composite structure 14 (see FIGS. 11,13) may comprise a rotorcraft composite structure on a rotorcraft, a watercraft composite structure on a watercraft, or another suitable composite structure 14.

Figure 14:
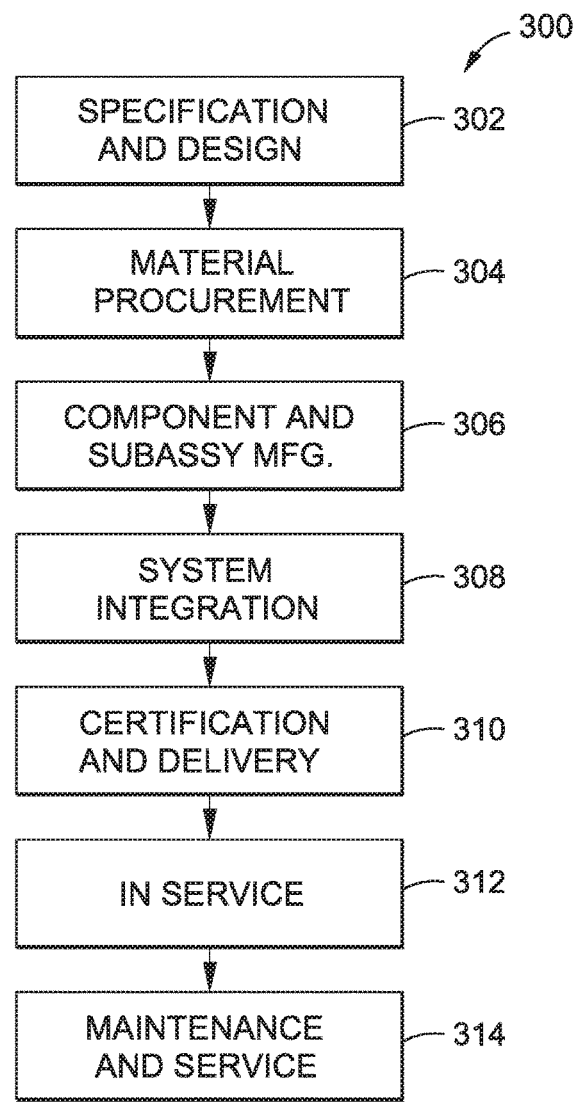
FIG. 14 is an illustration of a flow diagram of an exemplary aircraft manufacturing and service method.
Figure 15:
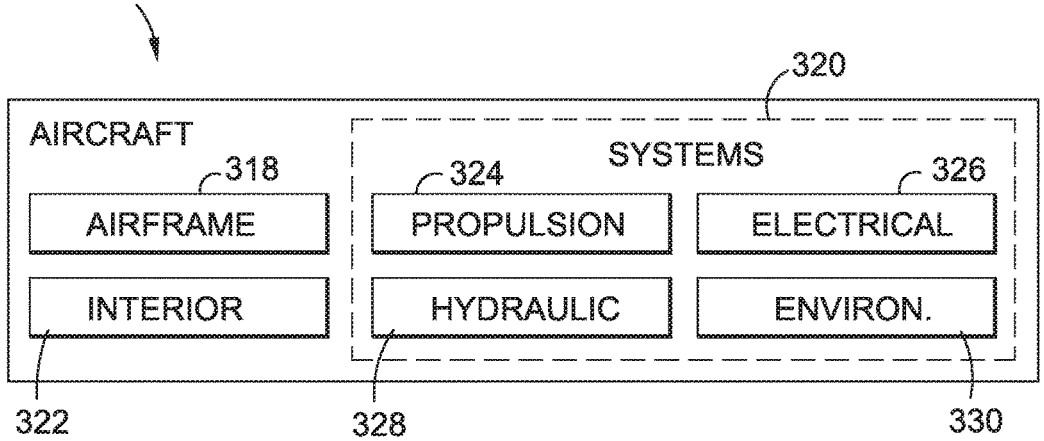
FIG. 15 is an illustration of an exemplary block diagram of an aircraft.

Referring now to FIGS. 14 and 15, FIG. 14 is an illustration of a flow diagram of an exemplary aircraft manufacturing and service method 300, and FIG. 15 is an illustration of an exemplary block diagram of an aircraft 316. Referring to FIGS. 14-15, embodiments of the disclosure may be described in the context of the aircraft manufacturing and service method 300 as shown in FIG. 14, and the aircraft 316 as shown in FIG. 15.

During pre-production, exemplary aircraft manufacturing and service method 300 may include specification and design 302 of the aircraft 316 and material procurement 304. During manufacturing, component and subassembly manufacturing 306 and system integration 308 of the aircraft 316 takes place. Thereafter, the aircraft 316 may go through certification and delivery 310 in order to be placed in service 312. While in service 312 by a customer, the aircraft 316 may be scheduled for routine maintenance and service 314 (which may also include modification, reconfiguration, refurbishment, and other suitable services).

Each of the processes of the aircraft manufacturing and service method 300 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 15, the aircraft 316 produced by the exemplary aircraft manufacturing and service method 300 may include an airframe 318 with a plurality of systems 320 and an interior 322. Examples of the plurality of systems 320 may include one or more of a propulsion system 324, an electrical system 326, a hydraulic system 328, and an environmental system 330. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 300. For example, components or subassemblies corresponding to component and subassembly manufacturing 306 may be fabricated or manufactured in a manner similar to components or subassemblies produced while the aircraft 316 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 316. Similarly, one or more of apparatus embodiments, method embodiments, or a combination thereof, may be utilized while the aircraft 316 is in service 312, for example and without limitation, to maintenance and service 314.

Disclosed embodiments of the removable chromatic witness assembly 10 (see FIGS. 1A-6), the removable chromatic witness system 100 (see FIGS. 8-10), and the method 160 (see FIG. 12), provide a removable chromatic witness applique 12 (see FIGS. 1A-6) used for multi-functional chromatic witness applications, that facilitates large scale manufacturing, ease of attachment and detachment, and provides a range of properties or types of chromatic materials 51 (see FIG. 8). The removable chromatic witness applique 12 (see FIGS. 1A-6) with the plurality of chromatic probes 50 (see FIG. 8) provides a way to apply the chromatic material 51 (see FIG. 8) continuously, evenly, and with full contact onto the surface 16 (see FIG. 8) of the composite structure 14 (see FIG. 8) to be tested and/or monitored, such as the inner wall of the thrust reverser 218 (see FIG. 13), and allows for easy removal and analysis. Moreover, the removable chromatic witness applique 12 (see FIGS. 1A-6) allows for temporary application to a composite structure 14 (see FIG. 8) to be tested and/or monitored, or to a structure from which the removable chromatic witness applique 12 (see FIGS. 1A-6) needs to be ultimately removed. Further, the removable chromatic witness applique 12 (see FIGS. 1A-6) with its individually separated or segmented chromatic witness geometric configurations 40 (see FIG. 8) enable a range of analysis approaches. In addition, the individually separated or segmented chromatic witness geometric configurations 40 (see FIG. 8) enable easier maintenance of individual segments or strips that may get damaged, and enable easier offline analysis of a given individual segment or strip. An additional advantage of the multiple segmented chromatic witness geometric configurations 40 (see FIG. 8) includes improved installation of the removable chromatic witness applique 12 (see FIGS. 1A-6) onto contoured surfaces without wrinkling or buckling.

In addition, disclosed embodiments of the removable chromatic witness assembly 10 (see FIGS. 1A-6), the removable chromatic witness system 100 (see FIGS. 8-10), and the method 160 (see FIG. 12), enable thermochromatic material 54a (see FIG. 8) or mechanochromatic material 56a (see FIG. 8) having different predefined time-temperature ranges 31 (see FIG. 8) to be laid out in an adjacent repeating arrangement 42a (see FIGS. 1A-3B) or nonadjacent repeating arrangement 42b (see FIG. 5), to each other to improve monitoring precision of the times 30 (see FIG. 8) and temperatures 26 (see FIG. 8) the composite structure 14 (see FIG. 8) are exposed to during testing and monitoring. Further, the removable chromatic witness applique 12 (see FIGS. 1A-6) is a multi-sensing applique 13 (see FIG. 8) that enables multi-sensing in a single applique with the multiple, different chromatic probes 50 (see FIG. 8), where each chromatic probe type is individually separated or segmented into separate chromatic witness geometric configurations 40 (see FIG. 8). Further, disclosed embodiments of the removable chromatic witness assembly 10 (see FIGS. 1A-6), the removable chromatic witness system 100 (see FIGS. 8-10), and the method 160 (see FIG. 12), provide a removable chromatic witness applique 12 (see FIGS. 1A-6) having standardized and multiple abilities to detect various types of possible issues, for example, thermal or impact damage, experienced by a composite structure 14 (see FIG. 8), such as thermal events 18 (see FIG. 8), for example, high heat, or impact events 20 (see FIG. 8), for example, mechanical impact stress.

Moreover, disclosed embodiments of the removable chromatic witness assembly 10 (see FIGS. 1A-6), the removable chromatic witness system 100 (see FIGS. 8-10), and the method 160 (see FIG. 12), enable large scale fabrication and rapid installation of the removable chromatic witness applique 12 (see FIGS. 1A-6) that is easily applied and removed, and that may be easily manufactured in sufficient quantities for effective use by test programs, such as testing of insulation blanket structure for thrust reverser inner walls of aircraft, and testing around aircraft engines, auxiliary power units (APUs), batteries, and other hardware or equipment that may experience thermal events 18 (see FIG. 8) or impact events 20 (see FIG. 8). This may decrease development costs of thermal blanket installation and evaluation during the aircraft flight testing. In turn, this may result cost savings on all future flight tests of thrust reversers.

Further, disclosed embodiments of the removable chromatic witness assembly 10 (see FIGS. 1A-6), the removable chromatic witness system 100 (see FIGS. 8-10), and the method 160 (see FIG. 12), may be used in the aerospace industry part during flight testing, ground testing, and/or in-service monitoring, as well as other industries, such as automotive, transportation, construction, ship building, and others, where thermal and mechanical impact testing is frequently conducted.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A removable chromatic witness assembly to monitor thermal events and impact events on a surface of a composite structure, the removable chromatic witness assembly comprising:
   a plurality of chromatic witness geometric configurations separately coupled in an arrangement to one or more portions of a polymeric film layer, each chromatic witness geometric configuration comprising a plurality of chromatic probes of a same type incorporated into an adhesive material, and at least two of the plurality of chromatic witness geometric configurations having a different type of chromatic probes with a different sensing capability for one of, thermal events and impact events on the surface of the composite structure, wherein the polymeric film layer and the plurality of chromatic witness geometric configurations form the removable chromatic witness assembly in a form of a removable chromatic witness applique configured to be removably applied directly and continuously to the surface of the composite structure, and configured to monitor the thermal events and the impact events on the surface of the composite structure.

2. The removable chromatic witness assembly of claim 1 further comprising a backing film layer and a pressure sensitive adhesive (PSA) layer, the backing film layer coupled to the plurality of chromatic witness geometric configurations, and the pressure sensitive adhesive (PSA) layer coupled to the backing film layer.

3. The removable chromatic witness assembly of claim 1 wherein the polymeric film layer is transparent and comprises a high temperature polymeric film layer that is stable in a temperature range of between about 130° F. (one hundred thirty degrees Fahrenheit) to about 500° F. (five hundred degrees Fahrenheit).

4. The removable chromatic witness assembly of claim 1 wherein the plurality of chromatic witness geometric configurations comprise three repeating chromatic witness geometric configurations, each of the three repeating chromatic witness geometric configurations having different types of chromatic probes.

5. The removable chromatic witness assembly of claim 1 wherein the plurality of chromatic witness geometric configurations are separately coupled in an adjacent repeating arrangement to the one or more portions of the polymeric film layer, and further wherein each chromatic witness geometric configuration has a geometric configuration comprising one of, a rectangular strip, and a square configuration.

6. The removable chromatic witness assembly of claim 1 wherein the plurality of chromatic probes comprise one of, thermochromatic probes and mechanochromatic probes.

7. The removable chromatic witness assembly of claim 1 wherein the adhesive material comprises a pressure sensitive adhesive (PSA) comprising one or more of a silicone adhesive, an acrylic adhesive, and an epoxy adhesive.

8. The removable chromatic witness assembly of claim 1 wherein the removable chromatic witness applique is a multi-sensing applique configured to take thermal testing measurements and impact testing measurements across the surface of the composite structure over which the removable chromatic witness applique is applied, and wherein after the composite structure is tested, the removable chromatic witness applique is configured to be removed and is configured to be analyzed.

9. A removable chromatic witness system to monitor thermal events and impact events on a surface of a composite structure to be tested and monitored, the removable chromatic witness system comprising:
the composite structure having the surface to be tested and monitored for one of, the thermal events and the impact events;
a removable chromatic witness assembly comprising a removable chromatic witness applique applied directly and continuously over the surface of the composite structure to be tested and monitored, the removable chromatic witness assembly comprising a plurality of chromatic witness geometric configurations separately coupled in a repeating arrangement to one or more portions of a polymeric film layer, each chromatic witness geometric configuration comprising a plurality of chromatic probes of a same type incorporated into an adhesive material, and at least two of the plurality of chromatic witness geometric configurations having a different type of chromatic probes with a different sensing capability for sensing one of, the thermal events and the impact events on the surface of the composite structure;
a light source configured to activate the plurality of chromatic probes in the removable chromatic witness applique applied on the surface of the composite structure, wherein each different type of chromatic probe is configured to fluoresce in a different predefined time-temperature range;
an imaging device configured to image and record one or more images of a chromatic response of the different types of chromatic probes to the light source, the chromatic response comprising one or more color changes and one or more intensity changes; and
a data processor system configured for processing and analyzing the one or more images to identify areas on the surface of the composite structure that have experienced one of, temperatures above a predefined threshold temperature, and impacts above a predefined threshold impact, based on the chromatic response.

10. The removable chromatic witness system of claim 9 wherein the removable chromatic witness assembly further comprises a backing film layer and a pressure sensitive adhesive (PSA) layer, the backing film layer coupled to the plurality of chromatic witness geometric configurations, and the pressure sensitive adhesive (PSA) layer coupled to the backing film layer.

11. The removable chromatic witness assembly of claim 9 wherein the plurality of chromatic witness geometric configurations comprise three repeating chromatic witness geometric configurations, each of the three repeating chromatic witness geometric configurations having different types of chromatic probes.

12. The removable chromatic witness system of claim 9 wherein the light source comprises one of, an ultraviolet (UV) light source, a light-emitting diode (LED) light source, and an infrared (IR) light source, and further wherein the imaging device comprises one of, a detector, including a spectrometer, and a camera, including a digital camera.

13. The removable chromatic witness system of claim 9 wherein the composite structure comprises an aircraft composite structure, and the removable chromatic witness applique is a multi-sensing applique configured to take thermal testing measurements and impact testing measurements across the surface of the composite structure over which the removable chromatic witness applique is applied, and wherein after the composite structure is tested, the removable chromatic witness applique is configured to be removed and is configured to be analyzed.

14. A method of using a removable chromatic witness system to monitor thermal events and impact events on a surface of a composite structure, the method comprising the steps of:
providing the removable chromatic witness system comprising:
the composite structure having the surface to be tested and monitored for one of, thermal events and impact events;
a removable chromatic witness assembly comprising a removable chromatic witness applique having a plurality of chromatic witness geometric configurations separately coupled in an arrangement to one or more portions of a polymeric film layer, each chromatic witness geometric configuration comprising a plurality of chromatic probes of a same type incorporated into an adhesive material, and at least two of the plurality of chromatic witness geometric configurations having a different type of chromatic probes with a different sensing capability for sensing one of, the thermal events and the impact events on the surface of the composite structure;

a light source;

an imaging device; and a data processor system;

applying the removable chromatic witness applique directly and continuously over the surface of the composite structure to be tested and monitored;

testing the composite structure with the applied removable chromatic witness applique, by exposing for a predefined time period the composite structure with the applied removable chromatic witness applique, to one of, one or more temperatures, and one or more impacts;

illuminating with the light source the removable chromatic witness applique, to activate the different types of chromatic probes to fluoresce in different predefined time-temperature ranges in response to the light source;

obtaining with the imaging device one or more images of a chromatic response of the different types of chromatic probes to the light source, the chromatic response comprising one or more color changes and one or more intensity changes; and using the data processor system to identify areas on the surface of the composite structure that have experienced one of, temperatures above a predefined threshold temperature, and impacts above a predefined threshold impact, based on the chromatic response.

15. The method of claim 14 further comprising after testing the composite structure with the applied removable chromatic witness applique and prior to illuminating with the light source, the step of removing the chromatic witness applique from the composite structure.

16. The method of claim 14 wherein providing the removable chromatic witness system comprises providing the removable chromatic witness applique with a backing film layer and a pressure sensitive adhesive (PSA) layer, the backing film layer coupled to the plurality of chromatic witness geometric configurations, and the pressure sensitive adhesive (PSA) layer coupled to the backing film layer.

17. The method of claim 14 wherein providing the removable chromatic witness system comprises providing the removable chromatic witness applique with three repeating chromatic witness geometric configurations, each of the three repeating chromatic witness geometric configurations having different types of chromatic probes configured to fluoresce in three different predefined time-temperature ranges.

18. The method of claim 14 further comprising, prior to testing the composite structure with the applied removable chromatic witness applique, conducting a calibration of the plurality of chromatic probes in the removable chromatic witness applique applied over the surface of the composite structure, using one or more thermocouples attached to the composite structure.

19. The method of claim 14 wherein testing the composite structure with the applied removable chromatic witness applique comprises testing an aircraft composite structure by conducting a test comprising one of, a flight test, a thermal test, and an impact test.

20. A method of making a removable chromatic witness assembly to monitor thermal events and impact events on a surface of a composite structure, the method comprising the steps of:

mixing a plurality of chromatic probes with an adhesive material to form separate chromatic witness geometric configurations, the plurality of chromatic probes comprising at least a first series of chromatic probes, a second series of chromatic probes, and a third series of chromatic probes;

applying a polymeric film layer over each of the chromatic witness geometric configurations to form multiple removable chromatic witness assemblies;

dividing each of the removable chromatic witness assemblies into multiple, separate rectangular strips;

applying the rectangular strips in an adjacent repeating arrangement over a backing film layer; and applying a pressure sensitive adhesive (PSA) layer to the backing film layer having the attached chromatic witness geometric configurations and the polymeric film layers to form the removable chromatic witness assembly comprising a removable chromatic witness applique, configured for application over the surface of the composite structure.

21. The method of claim 20 wherein the mixing the plurality of chromatic probes with the adhesive material to form separate chromatic witness geometric configurations comprises tailoring each of, the first series of chromatic probes, the second series of chromatic probes, and the third series of chromatic probes, to activate by exposure to one of, a temperature that exceeds a predefined threshold temperature, and an impact that exceeds a predefined threshold impact.

22. The method of claim 20 wherein the dividing each of the removable chromatic witness assemblies into multiple, separate rectangular strips comprises cutting each of the removable chromatic witness assemblies into multiple, separate rectangular strips having a width of about 0.5 inches or greater.

23. The method of claim 20 wherein the applying the rectangular strips in the adjacent repeating arrangement over the backing film layer comprises applying the rectangular strips over the backing film layer comprising a polymeric film layer that is stable in a temperature range of between about 130° F. to about 500° F.

24. The method of claim 20 wherein the applying the pressure sensitive adhesive (PSA) layer to the backing film layer to form the removable chromatic witness assembly comprises forming the removable chromatic witness applique in a tape form.

\* \* \* \* \*

UNITED STATES PATENT AND TRADEMARK OFFICE
CERTIFICATE OF CORRECTION

PATENT NO. : 10,024,792 B2  
APPLICATION NO. : 15/231691  
DATED : July 17, 2018  
INVENTOR(S) : Ryan E. Toivola et al.

Page 1 of 1

It is certified that error appears in the above-identified patent and that said Letters Patent is hereby corrected as shown below:

On the Title Page

Item (73) Assignee, Lines 1-2:
Please replace "Assignee: The Boeing Company, Chicago, IL (US)" with --Assignees: The Boeing Company, Chicago, IL (US); University of Washington, Seattle, WA (US)--

Signed and Sealed this  
Twenty-second Day of October, 2019

Andrei Iancu  
*Director of the United States Patent and Trademark Office*